(12) United States Patent
Seela et al.

(10) Patent No.: US 6,211,158 B1
(45) Date of Patent: Apr. 3, 2001

(54) DESAZAPURINE-NUCLEOTIDE DERIVATIVES, PROCESSES FOR THE PREPARATION THEREOF, PHARMACEUTICAL COMPOSITIONS CONTAINING THEM AND THE USE THEREOF FOR NUCLEIC ACID SEQUENCING AND AS ANTIVIRAL AGENTS

(75) Inventors: Frank Seela, Paderborn; Heinz-Peter Muth, Osnabrück; Klaus Kaiser, Osnabrück; Werner Bourgeois, Osnabrück; Klaus Mühlegger, Polling; Herbert Von der Eltz, Weilheim; Hans-Georg Batz, Tutzing, all of (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 07/908,513

(22) Filed: Jun. 26, 1992

Related U.S. Application Data

(63) Continuation-in-part of application No. 07/179,862, filed on Apr. 11, 1988, now abandoned.

(30) Foreign Application Priority Data

Apr. 14, 1987 (DE) ................ 37 12 280
Nov. 20, 1987 (DE) ................ 37 39 366

(51) Int. Cl.[7] ............ A01N 43/04; C07H 19/04
(52) U.S. Cl. .................. 514/44; 536/26.1
(58) Field of Search ............... 536/23.1, 25.6, 536/26.1, 26.21, 26.26; 544/262, 264; 514/44, 45, 46

(56) References Cited

U.S. PATENT DOCUMENTS

| | | | |
|---|---|---|---|
| 3,364,198 | * 1/1968 | Wiley | 536/24 |
| 3,962,211 | * 6/1976 | Townsend et al. | 536/24 |
| 4,299,824 | * 11/1981 | Rideout et al. | 536/24 |
| 4,315,000 | 2/1982 | Cook | 424/180 |
| 4,439,604 | * 3/1984 | Cook | 536/24 |
| 4,719,295 | * 1/1988 | Cook et al. | 536/24 |
| 4,804,748 | * 2/1989 | Seela | 536/24 |
| 4,892,865 | 1/1990 | Townsend et al. | 514/43 |
| 4,920,210 | 4/1990 | Koszalka et al. | 536/24 |
| 5,047,519 | 9/1991 | Hobbs, Jr. et al. | 536/23 |

FOREIGN PATENT DOCUMENTS 251786   1/1988   (EP) .
63-130599   6/1988   (JP) .

OTHER PUBLICATIONS

Mizusawa et al. (1986) Nucleic Acids Research, vol. 14, No. 3, pp. 1319–1324.*
Girgis et al., Nucl. Acids Res. 16: 1217–1226 (1987).
Mizusawa et al., Nucl. Acids Res. 14: 1319–1324 (1986).
Gupta et al., H. Het. Chem. 23: 59–64 (1986).
Kazimierczuk et al., J. Am. Chem. Soc. 106: 6379–6382 (1984).
Robins et al., Can. J. Chem. 55: 1251–1259 (1977).
Jain et al., J. Org. Chem. 38(18): 3179–3186 (1973).

* cited by examiner

Primary Examiner—Elizabeth F. McElwain
(74) Attorney, Agent, or Firm—Fulbright & Jaworski, LLP

(57) ABSTRACT

The present invention provides desazapurine-nucleoside derivatives of the general formula:

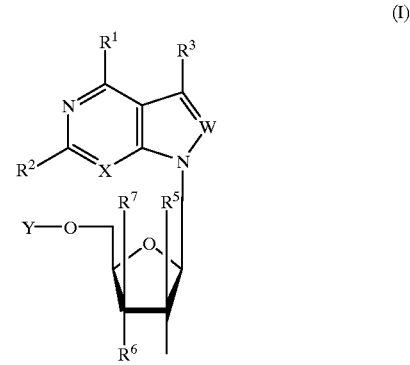

(I)

wherein X is a nitrogen atom or a methine radical, W is a nitrogen atom or a C—$R^4$ radical, $R^1$, $R^2$, $R^3$ and $R^4$, which can be the same or different, are hydrogen or halogen atoms, hydroxyl or mercapto groups, lower alkyl, lower alkylthio, lower alkoxy, aralkyl, aralkoxy or aryloxy radicals or amino groups optionally substituted once or twice, $R^5$ is a hydrogen atom or a hydroxyl group, $R^6$ and $R^7$ are each hydrogen atoms or one of them is a halogen atom or a cyano or azido group or an amino group optionally substituted once or twice, whereby one of $R^6$ and $R^7$ can also be a hydroxyl group when X is a methine radical and, in addition, $R^5$ and $R^7$ can together also represent a further valency bond between C-2' and C-3' and Y is a hydrogen atom or a mono-, di- or tri-phosphate group.

2 Claims, No Drawings

DESAZAPURINE-NUCLEOTIDE DERIVATIVES, PROCESSES FOR THE PREPARATION THEREOF, PHARMACEUTICAL COMPOSITIONS CONTAINING THEM AND THE USE THEREOF FOR NUCLEIC ACID SEQUENCING AND AS ANTIVIRAL AGENTS

RELATED APPLICATION

This application is a continuation-in-part of Ser. No. 07/179,862, filed Apr. 11, 1988, and now abandoned.

The present invention is concerned with new desazapurine-nucleoside derivatives, processes for the preparation thereof, as well as the use thereof in the sequencing of nucleic acids, and also as anti-viral agents. The compounds of the invention are characterized by enhanced stability as compared to 2',3'-dideoxy compounds, which can easily be hydrolyzed under acidic conditions. The compounds of the invention are not so easily hydrolyzed.

The new desazapurine-nucleoside derivatives according to the present invention are compounds of the general formula:

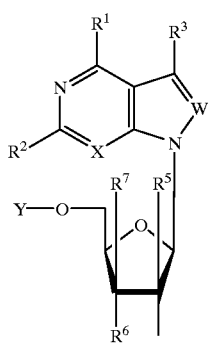

(I)

wherein X is a nitrogen atom or a methine group, W is a nitrogen atom or a C-$R^4$ radical, $R^1$, $R^2$, $R^3$ and $R^4$, which can be the same or different, are hydrogen or halogen atoms, hydroxyl or mercapto groups, lower alkyl, lower alkylthio, lower alkoxy, aralkyl, aralkoxy or aryloxy radicals or amino groups optionally substituted once or twice, $R^5$ is a hydrogen atom or a hydroxyl group and $R^6$ and $R^7$ are each hydrogen atoms or one of them is a halogen atom or a cyano or azido group or an amino group optionally substituted once or twice, whereby one of $R^6$ and $R^7$ can also be a hydroxyl group when X is a methine radical and, in addition, $R^5$ and $R^7$ can together represent a further valency bond between C-2' and C-3' and Y is a hydrogen atom or a mono-, di- or triphosphate group, as well as the tautomers and salts thereof and nucleic acids which contain compounds of general formula I as structural components.

The lower alkyl radicals in the definition of the substituents $R^1$, $R^2$, $R^3$ and $R^4$ can be saturated or unsaturated, straight-chained or branched and contain up to 7 and preferably up to 4 carbon atoms. This definition of the alkyl radicals also applies to the alkyl moieties which occur in the definitions of the lower alkylthio and lower alkoxy radicals. The methyl and ethyl radicals are quite especially preferred.

By halogen in the definition of the substituents $R^1$, $R^2$, $R^3$, $R^4$, $R^6$ and $R^7$ are to be understood fluorine, chlorine, bromine and iodine.

The aralkyl and aralkoxy radicals in the definitions of the substituents $R^1$, $R^2$, $R^3$ and $R^4$ contain an alkyl moiety with up to 5 and preferably with up to 3 carbon atoms which are substituted one or more times with an arylmoiety suitably of 6 to 10 carbon atoms, for example a phenyl or naphthyl radical. The aromatic radicals can, in turn, be substituted one or more times by an alkyl or alkoxy radical. The benzyl radical is especially preferred.

As aryloxy radical in the definition of $R^1$, $R^2$, $R^3$ and $R^4$, the phenyloxy radical is especially preferred which can optionally be substituted one or more times by further substituents, for example nitro groups and alkyl and alkoxy radicals.

The amino group occurring in the definition of $R^1$, $R^2$, $R^3$, $R^4$, $R^6$ and $R^7$, which can optionally be substituted once or twice, contains, as possible substituents, preferably alkyl radicals with up to 5 and preferably up to 3 carbon atoms which, in turn, can be substituted by alkoxy radicals, halogen atoms or amino groups optionally substituted once or twice. These substituents can also represent an aralkyl radical. The two nitrogen substituents can together also represent an alkylidene radical and preferably a methylidene radical which, in turn, can be substituted by alkoxy, substituted amino groups or halogen atoms. A quite especially preferred substituent of this kind is the dimethylaminomethylidene radical.

The monophosphate group is the —PO(OH)$_2$ group, the diphosphate group is the —P$_2$O$_3$(OH)$_3$ group and the triphosphate group is the P$_3$O$_5$(OH)$_4$ group.

As possible salts, there are especially preferred the alkali metal, alkaline earth metal and ammonium salts of the phosphate groups. The alkaline earth metal salts are especially the magnesium and calcium salts. By ammonium salts, according to the present invention there are to be understood salts which contain the ammonium ion which can be substituted up to four times by alkyl radicals containing up to 4 carbon atoms and/or by aralkyl radicals, preferably the benzyl radical. The substituents can hereby be the same or different. The salts of the phosphates can be converted in known manner into the free acids.

The compounds of general formula I can contain basic groups, especially amino groups, which can be converted into acid addition salts with appropriate acids. As acids for this purpose, there can be used, for example, hydrochloric acid, hydrobromic acid, sulphuric acid, phosphoric acid, fumaric acid, succinic acid, tartaric acid, citric acid, lactic acid, maleic acid and methanesulphonic acid.

The compounds of general formula I are new. They can be prepared analogously to known, related compounds. For the preparation of the compounds of general formula I, a process has proved to be especially preferred in which a compound of the general formula:

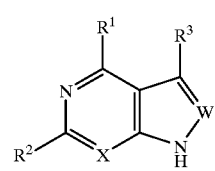

(II)

in which X, W, $R^1$, $R^2$ and $R^3$ have the same meanings as above, is reacted with a compound of the general formula:

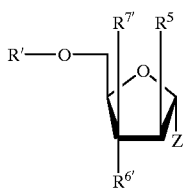

(III)

in which R⁵ has the above-given meaning, R⁶' and R⁷' each represent hydrogen atoms or one of these two symbols represents an azido group or a hydroxyl group protected by an oxygen protection group, R' is an oxygen protection group and Z is a reactive group, to give a compound of the general formula:

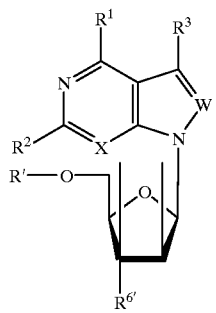

(IV)

in which X, W, R¹, R², R³, R⁵, R⁶', R⁷' and R' have the above-given meanings, and oxygen protective groups possibly present are split off and thereafter a compound thus obtained, in which R⁶ or R⁷ is a hydroxyl group, after selective protection of the 5'-hydroxyl group, is optionally converted with a halide, cyanide or azide in known manner into a compound of general formula I in which R⁶ or R⁷ is a halogen atom or a cyano or azido group or, in known manner, is deoxygenated to give a compound of general formula I, in which R⁶ or R⁷ is a hydrogen atom or a compound thus obtained of general formula I, in which R⁶ or R⁷ is an azido group, is reduced in known manner to a compound of general formula I in which R⁶ or R⁷ is an amino group and, if desired, a compound of general formula I, in which Y is a hydrogen atom, is converted in known manner into a mono-, di- or tri-phosphate and, if desired, a free base or acid obtained is converted into an appropriate salt or a salt obtained is converted into the corresponding free base or acid.

The compounds of general formula II are reacted with the compounds of general formula III especially advantageously under phase transfer conditions. Under the conditions of phase transfer catalysis, the bases of general formula II are converted into a corresponding anion, for example by means of a 50% aqueous solution of sodium hydroxide. The anion thus obtained is hydrophobed by a phase transfer catalyst, for example tris-[2-(2-methoxyethoxy)-ethyl]-amine, and transported into the organic phase in which it reacts with the reactive compound of general formula III.

As reactive groups Z in the compounds of general formula III, there are preferably used halogen atoms and alkoxy radicals. In the case of this reaction, the hydroxyl groups of the sugar residue are protected in the usual way by conventional oxygen protective groups, for example toluoyl, benzoyl or acetyl radicals. After completion of the reaction, the oxygen protective groups can again be split off in known manner under alkaline conditions, a 1M methanolic menthanolate solution preferably being used.

During the reaction, it is preferable to keep the radicals R¹, R², R³ and R⁴ protected by appropriate protective groups.

Another advantageous method for the preparation of compounds of general formula IV is the solid-liquid phase transfer process with the use of solid, powdered potassium hydroxide, the above-mentioned phase transfer catalyst, as well as compounds of general formulae II and III in an aprotic solvent.

Compounds of general formula I, in which R⁶ or R⁷ is a halogen atom or an azido group, are preferably prepared by starting from a compound of general formula I, in which R⁶ or R⁷ is a hydroxyl group. The hydroxyl group in the 5'-position is first to be selectively protected. For this purpose, too, known processes are available. For example, in nucleotide chemistry, the 4,4'-dimethoxy-triphenylmethyl radical has proved to be useful. After the reaction has taken place, this can again be easily split off by mild acid hydrolysis, whereas the also acid-labile glycosidic bond is not hydrolysed under these conditions. The reaction of the nucleoside to be protected with the oxygen protective group reagent for the 5'-hydroxyl group is carried out in an appropriate organic solvent, preferably in dry pyridine, with a small excess of the oxygen protective group reagent, as well as possibly of an appropriate adjuvant base, for example N-ethyldiisopropylamine. The so protected compound of general formula I is reacted with a halide, preferably with an alkali metal halide or an organic halide, or with an azide, preferably with an alkali metal azide, in known manner. The hydroxyl group on the C-3' atom is thereby nucleophilically substituted by the halide or azide.

Compounds of general formula I, in which R⁶ or R⁷ is a hydroxyl group, can also, after previous protection of the 5'-hydroxyl group in the above-described manner, be desoxygenated by known methods to give compounds of general formula I, in which R⁶ and R⁷ are hydrogen atoms. For this purpose, the compound of general formula I, in which R⁶ or R⁷ is a hydroxyl group and in which the 5'-hydroxyl group has been protected in the above-described way and other functional radicals also carry protective groups, is first converted into a 3'-O-thiocarbonyl derivative which is subsequently reduced radically with tributyl tin hydride. Such methods for the deoxygenation of 2'-deoxynucleosides to give 2',3'-dideoxynucleosides are known, the Barton deoxygenation method having proved to be especially favourable (J. Chem. Soc., Perkin Trans. I (1975), 1574).

Compounds of general formula I, in which R⁶ or R⁷ is an amino group, are preferably prepared by reducing a compound of general formula I, in which the substituent R⁶ or R⁷ is an azido group. This reduction of the azido group to the amino group can be carried out by various generally known methods, the reduction with hydrogen in the presence of a palladium-charcoal catalyst having proved to be especially advantageous.

The phosphate groups are introduced into compounds of general formula I, in which Y is a hydrogen atom, in known manner. The monophosphates are obtained, for example, by phosphorylating compounds of general formula I, in which Y is a hydrogen atom, with phosphorus oxychloride in trimethyl phosphate. The triethylammonium salts obtained in this way can be converted in known manner into other salts by transsalification. The di- and triphosphates are obtained according to known methods, preferably from the monophosphates, by reaction with orthophosphates or pyrophosphates. Their various salts can also be prepared by known methods.

Compounds of general formula II are either known or can be prepared analogously to known compounds. Such methods of preparation are described, for example, in Chemische Berichte, 110, 1462/1977; J. Chem. Soc.; 1960, 131; and Tetrahedron Letters, 21, 3135/1980.

Some of the compounds of general formula III are also known. Compounds which have not hitherto been described can be prepared completely analogously to the known compounds. The preparation of such compounds is described, for example, in Chem. Ber., 93, 2777/1960 and in Synthesis, 1984, 961.

The new compounds according to the present invention possess valuable pharmacological properties. In particular, by inhibition of the enzyme reverse transcriptase, the multiplication of retroviruses is prevented, i.e. the compounds according to the present invention possess especially cytostatic, as well as antiviral properties.

The structural units of nucleic acids contain, as glycosidic components, either the β-D-ribofuranosyl radical or the deoxy derivative thereof. Besides these aglyconic radicals, modified D-ribofuranosyl derivatives are also found in nucleoside antibiotics. Thus, for example cordycepin, which can be isolated from culture filtrates of *Cordyceps militaris,* contains the monosaccharide cordycepose. Besides this 2'- or 3'-deoxy derivative of the ribonucleosides, some considerable time ago, 2',3'-didesoxynucleosides have been prepared synthetically. They have anti-viral action and can, in particular, via the inhibition of the enzyme reverse transcriptase, inhibit the multiplication of retroviruses (cf. Proc. Natl. Acad. Sci. USA, 83, 1911/1986 and Nature, 325, 773/1987). The inhibitory action on the HIV virus, the cause of AIDS, is of especial therapeutic interest. However, they have the disadvantage that they are also inhibitors of cellular DNA polymerase so that they act cytotoxically. Furthermore, they can be deactivated by cellular enzymes. The compounds of general formula I do not display these disadvantages. They have antiviral action without being cytotoxic.

The compounds of general formula I according to the present invention can also be advantageously used for DNA sequencing according to Sanger's method. The sequencing of d(G-C)-rich DNA fragments is, in particular, made difficult by the formation of secondary structures which lead to a band compression in the region of d(G-C) clusters. The reason for this is the Hoogsteen base pairing of guanosine molecules. By means of the replacement of 2'-deoxyguanosine triphosphate by the compounds according to the present invention, in which $R^6$ is a hydroxyl group, the band compression is largely overcome.

The compounds of general formula I according to the present invention, in which $R^6$ and $R^7$ are hydrogen atoms, are used in DNA sequencing by Sanger's method as chain terminators instead of the known 2',3'-dideoxy compounds.

Nucleic acids which, as structural components, contain one or more compounds of general formula I, can be prepared according to known processes (for example as described in Nucleic Acids Research, 14(5), 2319 et seq./ 1986). However, they also result, for example, in the case of the DNA sequencing. If compounds of general formula I, in which $R^6$ is a hydroxyl group, are used as structural components, then a nucleic acid can contain several such structural components; if, as structural component, a compound of general formula I is used, in which $R^6$ is a hydrogen atom, then such a structural component can only be incorporated once, namely, on the end of the chain. The nucleic acids according to the present invention are made up of 2 to 1000 and preferably of 8 to 50 nucleotide structural components, nucleic acids with 15 to 30 nucleotide structural components being especially preferred.

These nucleic acids can also be used as antiviral agents. These nucleic acids hybridise with the ssDNA/RNA of the virus and make difficult the transcription to the virus DNA. Such nucleic acids can be used especially as agents against the HIV virus since they are not decomposed or only decomposed with difficulty by the cell's own restriction enzymes.

For the preparation of pharmaceutical compositions, the compounds of general formula I, the pharmacologically acceptable salts thereof or nucleic acids containing them are mixed in known manner with appropriate pharmaceutical carrier substances, aroma, flavouring and colouring materials and formed, for example, into tablets or dragees or, with the addition of appropriate adjuvants, are suspended or dissolved in water or an oil, for example olive oil.

The compounds according to the present invention can be administered enterally or parenterally in liquid or solid form. As injection medium it is preferred to use water which contains the additives usual in the case of injection solutions, such as stabilizing agents, stabilizing agents and/or buffers.

Such additives include, for example, tartrate and citrate buffers, ethanol, complex formers (such as ethylenediaminetetraacetic acid and the non-toxic salts thereof) and high molecular weight polymers (such as liquid polyethylene oxide) for viscosity regulation. Solid carrier materials include, for example, starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavouring and sweetening agents.

The compounds according to the present invention are usually administered in an amount of from 1 to 100 mg. and preferably of from 2 to 80 mg. per day per kg. body weight. It is preferred to divide up the daily dose into 2 to 5 administrations, in which case each administration comprises 1 or 2 tablets with a content of active material of from 5 to 1000 mg. The tablets can also be formulated as a controlled release form, in which case the number of administrations per day can be reduced to from 1 to 3. The active material content of the retarded tablets can be from 20 to 2000 mg. The active material can also be administered by injection one to eight times per day or by continuous infusion, in which case amounts of from 500 to 4000 mg./day normally suffice.

The following Examples are given for the purpose of illustrating the present invention:

EXAMPLE 1

2-Amino-7-deaza-2',3'-dideoxy-9-β-D-ribofuranosylpurine-6-one a) 2-[(4,4'-Dimethoxytriphenylmethyl)-amino]-7-desaza-2'-deoxy-5'-O-(4,4'-dimethoxytriphenylmethyl)-9-β-D-ribofuranosylpurine-6-one 1.0 g. (3.8 mMole) 7-deaza-2'-desoxyguanosine is evaporated twice with dry pyridine and then suspended in 20 ml. pyridine. 4.0 g. (11.8 mMole) 4,4'-dimethoxytriphenylmethyl chloride and 2.5 ml. (14.6 mMole) Hünig base (N-ethyldiisopropylamine) are added thereto and the reaction mixture is stirred for 3 hours at ambient temperature.

The reaction mixture is subsequently introduced into 150 ml. of a 5% aqueous solution of sodium bicarbonate and extracted twice with 150 ml. amounts of dichloromethane. The combined organic extracts are dried over anhydrous sodium sulphate, filtered and chromatographed on silica gel 60 H (column 10×4 cm., dichloromethane/acetone 9:1 v/v). After evaporation of the main zone, the residue is dissolved in a little dichloromethane and added dropwise to a mixture of n-hexane/diethyl ether (1:1 v/v). After filtration, there are obtained 2.04 g. (61% of theory) of the desired colourless, amorphous compound. TLC (silica gel, dichloromethane/acetone (8:2 v/v): $R_f$=0.7; UV (methanol: $\lambda_{max}$=272, 283 nm (shoulder) ($\epsilon$=18800, 16400).

$^1$H-NMR ([$D_6$]DMSO): δ=1.75 (m, 2'-Hb), 1.86 (m, 2'-$H_a$); 3.09 (m, 5'-H), 3.79 (m, 4'-H), 4.10 (m, 3'-H), 5.19 (d, 3'-OH, J=4.3 Hz), 5.61 (pt, 1'-H, J=6.5 Hz), 6.16 (d, 6-H, J=3.5 Hz), 6.62 (d, 5-H, J=3.5 Hz), 10.35 (s, NH).

Analysis for $C_{53}H_{50}N_4O_8$ (M.W. 871.0) calc.: C, 73.07; H, 5.79; N, 6.43; found: 73.02; 5.98; 6.34.

b) 2-[(4,4'-Dimethoxytriphenylmethyl)-amino]-7-deaza-2'-deoxy-3'-O-phenoxythiocarbonyl-5'-O-(4,4'-dimethoxy-triphenylmethyl)-9-β-D-ribofuranosylpurine-6-one A suspension of 1.0 g. (1.1 mMole) of the compound of 1a) in 15 ml. dry acetonitrile is mixed with 300 mg. (2.5 mMole) p-dimethylaminopyridine and 300 μl. (2.2 mMole) phenoxythiocarbonyl chloride and stirred for 16 hours at ambient temperature. The reaction mixture is evaporated and the residue chromatographed on a silica gel 60 H column (column 10×4 cm., dichloromethane/acetone; 8:2 v/v). The residue obtained by evaporation of the main zone is dissolved in a little dichloromethane and precipitated out by the dropwise addition of a mixture of n-hexane/diethyl ether (1:1 v/v) to give 0.99 g. (89% of theory) of a colourless, amorphous substance. TLC (silica gel, methylene dichloride/acetone (8:2 v/v): $R_f$=0.8; UV (methanol): $\lambda_{max}$=269, 282 nm (shoulder) ($\epsilon$=19300, 16000).

$^1$H-NMR ([$D_6$]DMSO): δ=2.06 (m, 2'-$H_b$), 2.34 (m, 2'-$H_a$), 3.26 (m, 5'-H), 4.25 (m, 4'-H), 5.61 (m, 3'-H and 1'-H), 6.23 (d, 6-H, J=3.5 Hz), 6.67 (d, 5-H, J=3.5 Hz), 10.41 (s, NH).

Analysis for $C_{60}H_{54}N_4O_9S$ (M.W. 1007.2)
calc.: C, 71.77; H, 5.40; N, 5.56; S, 3.18;
found: 71.26; 5.43; 5.52; 3.11.

c) 2-[(4,4'-Dimethoxytriphenylmethyl)-amino]-7-deaza-2',3'-dideoxy-5'-O-(4,4'-dimethoxytriphenylmethyl)-9-β-D-ribofuranosylpurine-6-one 500 mg. (0.5 mMole) of the compound of lb) in 20 ml. freshly distilled toluene are mixed with 30 mg. (0.2 mMole) 2,2'-azo-bis-(2-methylpropionic acid nitrile) and 300 μl. (1.1 mMole) tributyl tin hydride and stirred for 3 hours under an atmosphere of argon at 80° C. (TLC monitoring, chloroform/methanol 97:3 v/v). After completion of the reaction, the reaction mixture is evaporated and the residue chromatographed on silica gel 60 H (column 30×4 cm.; dichloromethane/methanol 99:1 v/v). After evaporation of the main zone and taking up in a little dichloromethane, 320 mg. (75% of theory) of the desired amorphous, colourless compound is precipitated out by dropping into n-hexaneldiethyl ether. TLC (silica gel, methylene chloride/methanol, 95:5 v/v): $R_f$=0.5.

$^1$H-NMR ([$D_6$]DMSO): δ1.63, 1.80 (2 m, 2'-H and 3'-H), 3.07 (m, 5'-H), 4.06 (m, 4'-H), 5.43 (m, 1'-H), 6.11 (d, 6-H, J=3.5 Hz), 6.65 (d, 5-H, J=3.5 Hz), 10.34 (s, NH).

d) 2-Amino-7-deaza-2',3'-dideoxy-9-β-D-ribofuranosylpurine-6-one 300 mg. (0.35 mMole) of the compound from 1c) are dissolved in 10 ml. 80% acetic acid and stirred for 15 minutes at ambient temperature. Subsequently, the solvent is stripped off at oil pump vacuum and the residue evaporated several times with water. The crude product is chromatographed on silica gel 60H (column 10×4 cm., dichloromethane/methanol 9:1 v/v). The foamy substance obtained by evaporation of the main fraction is crystallised from a little methanol to give 50 mg. (57% of theory) of colourless needles; m.p. 228° C. (decomp.). TLC (silica gel, dichloromethane/methanol 9:1 v.v): $R_f$=0.3.

UV (methanol): $\lambda_{max}$=261, 281 nm (shoulder) ($\epsilon$=13300, 7800).

$^1$H-NMR ([$D_6$]DMSO): δ=1.96 (m, 3'-H), 2.08, 2.27 (2 m, 2'-$H_a$ and 2'-$H_b$), 3.48 (m, 5'-H), 3.97 (m, 4'-H), 4.86 (t, 5'-OH, J=5.4 Hz), 6.12 (pt, 1'-H, J=5.5 Hz), 6.24 (m, $NH_2$ and 6-H), 6.92 (d, 5-H, J=3.5 Hz), 10.34 (s, NH).

Analysis for $C_{11}H_{14}N_4O_3$ (M.W. 250.3) calc.: C, 52.79; H, 5.64; N, 22.39; found: 52.98; 5.80; 22.55.

In an analogous manner, via the corresponding 2'-deoxynucleosides and subsequent deoxygenation as in c), there are obtained the following compounds:

A) 3,7-dideaza-2',3'-dideoxy-9-β-D-ribofuranosylpurine

UV (0.1 N HCl): $\lambda_{max}$=224, 274 nm

Analysis for $C_{12}H_{14}N_2O_2$ (M.W. 218.2) calc.: C, 66.0; H, 6.4; N, 12.8; found: 66.1; 6.4; 12.6.

B) 3,7-dideaza-2',3'-dideoxy-9-β-D-ribofuranosylpurine-6-one

UV (methanol): $\lambda_{max}$=264 nm ($\epsilon$=11600), 282 nm ($\epsilon$=8000), 295 nm ($\epsilon$=5200)

Analysis for $C_{12}H_{14}N_2O_3$ (M.W. 234.2) calc.: C, 61.5; H, 6.0; N, 11.95; found: 61.3; 6.1; 11.8.

C) 2-chloro-6-methoxy-3,7-dideaza-2',3'-dideoxy-9-β-D-ribofuranosylpurine

UV (methanol): $\lambda_{max}$=271, 280 nm

Analysis for $C_{13}H_{15}N_2O_3Cl$ (M.W. 282.6) calc.: C, 55.2; H, 5.3; N, 9.9; found: 55.1; 5.3; 9.9.

D) 6-amino-3,7-dideaza-2',3'-dideoxy-9-β-D-ribofuranosylpurine

Analysis for $C_{12}H_{15}N_3O_2$ (M.W. 233.2) calc.: C, 63.65; H, 6.16; N, 17.13; found: 63.62; 6.11; 17.01.

UV (methanol) $\lambda_{max}$=271 nm ($\epsilon$=12800)

E) 3,7-dideaza-2',3'-dideoxy-9-β-D-ribofuranosylpurine-2,6-dione

Analysis for $C_{12}H_{14}N_2O_4$ (M.W. 250.2) calc.: C, 57.55; H, 5.6; N, 11.2; found: 57.50; 5.7; 11.2.

EXAMPLE 2

2-{[(Dimethylamino)-methylene]-amino}-7-deaza-2',3'-dideoxy-9-β-D-ribofuranosylpurine-6-one a) 2-[(Dimethylamino)-methylene]-amino-7-desaza-2'-deoxy-9-β-D-ribofuranosylpurine-6-one 270 mg. (1.01 mMole) 7-deaza-2'-deoxyguanosin in 5 ml. dry, amine-free dimethylformamide are mixed with 2 ml.

(11.7 mMole) N,N-dimethylformamide diethyl acetal and stirred for 1 hour at 50° C. under an atmosphere of argon. Subsequently, the reaction mixture is evaporated in a vacuum and the residue chromatographed on silica gel 60 H (column 10×4 cm., dichloromethane/methanol 9:1 v/v). By evaporation of the solvent, from the main zone there are obtained 230 mg. (71% of theory) of a pale yellow, amorphous substance. TLC (silica gel, dichloromethane/methanol 9:1 v/v): $R_f$=0.3.

UV (methanol): $\lambda_{max}$=240, 311 nm ($\epsilon$=18300, 17400).

$^1$H-NMR ([D$_6$]DMSO: δ=2.15 (m, 2'-H$_b$), 2.41 (m, 2'-H$_a$), 3.02, 3.15 (s, 2 CH$_3$), 3.52 (m, 5'-H), 3.79 (m, 4'-H), 4.32 (m, 3'-H), 4.91 (t, 5'-OH, J=5.4 Hz), 5.27 (d, 3'-OH, J=3.5 Hz), 6.34 (d, 6-H, J=3.5 Hz), 6.45 (pt, 1'-H, J=7.0 Hz), 7.07 (d, 5-H, J=3.5 Hz), 8.56 (s, NH=C), 11.04 (s, NH).

Analysis for C$_{14}$H$_{19}$N$_5$O$_4$ (M.W. 321.3) calc.: C, 52.33; H, 5.96; N, 21.79; found: 52.48; 6.14; 21.69.

b) 2-{[(Dimethylamino)-methylene]-amino}-7-deaza-2'-deoxy-5'-O-(4,4'-dimethoxytriphenylmethyl)-9-β-D-ribofuranosylpurine-6-one 100 mg. (0.31 mMole) of the compound from 2a) are dissolved in 2 ml. dry pyridine, mixed with 170 mg. (0.5 mMole) 4,4'-dimethoxytriphenylmethyl chloride and 0.2 ml. (1.2 mMole) Hünig base and stirred for 3 hours at ambient temperature. Subsequently, the reaction mixture is evaporated and the residue chromatographed on silica gel 60 H (column 10×2.5 cm., elution agent chloroform/methanol 99:1 v/v). The residue obtained by evaporation of the main fraction is dissolved in methylene chloride and, by dropping into a mixture of n-hexane/diethyl ether (1:1 v/v), 160 mg. (84% of theory) of a colourless, amorphous substance are precipitated out. TLC (silica gel, methylene chloride/methanol 9:1 v/v): $R_f$=0.6.

UV (methanol): $\lambda_{max}$236, 311 nm ($\epsilon$=38200, 18100).

$^1$H-NMR ([D$_6$]DMSO): δ=2.23 (m, 2'-H$_b$), 2.42 (m, 2'-H$_a$), 3.03 (s, CH$_3$), 3.14 (m, 5'-H and CH$_3$), 3.90 (m, 4'-H), 4.33 (m, 3'-H), 5.34 (d, 3'-OH, J=4.3 Hz), 6.34 (d, 6-H, J=3.5 Hz), 6.49 (pt, 1'-H, J=6.8 Hz), 6.90 (d, 5-H, J=3.5 Hz), 8.58 (s, NH=C), 11.07 (s, NH).

Analysis for C$_{35}$H$_{37}$N$_5$O$_6$ (M.W. 623.7) calc.: C, 67.40; H, 5.98; N, 11.23; found: 67.31; 6.00; 11.17.

c) 2-{[(Dimethylamino)-methylene]-amino}-7-deaza-2'-deoxy-3'-O-phenoxythiocarbonyl-5'-O-(4,4'-dimethoxy-triphenylmethyl)-9-β-D-ribofuranosylpurine-6-one 900 mg. (1.4 mMole) of the compound from 2b), dissolved in 15 ml. dry dichloromethane, are mixed with 340 mg. (2.8 mMole) p-dimethylaminopyridine and 250 μl. (1.8 mMole) phenoxythiocarbonyl chloride and stirred for 16 hours at ambient temperature. The solution is evaporated in a vacuum and the residue chromatographed on silica gel 60 H (column 20×4 cm., chloroform/acetone 7:3 v/v). The residue obtained by evaporation of the main zone is taken up in a little dichloromethane and the desired colourless, amorphous compound precipitated out by dropping into n-hexane/diethyl ether (1:1 v/v). TLC (silica gel, methylene chloride/methanol 95:5 v/v): $R_f$=0.5.

UV (methanol): $\lambda_{max}$=235, 277 (shoulder), 283, 312 nm ($\epsilon$=41300, 11400, 12600, 17000).

$^1$H-NMR ([D$_6$]DMSO): δ=2.73 (m, 2'-H$_b$), 2.97 (m, 2'-H$_a$), 3.01, 3.10 (s, 2 CH$_3$), 3.37 (m, 5'-H), 4.33 (m, 4'-H), 5.90 (m, 3'-H), 6.40 (d, 6-H, J=3.5 Hz), 6.55 (pt, 1'-H), 6.98 (d, 5-H, J=3.5 Hz), 8.58 (s, CH=N), 11.30 (s, NH).

Analysis for C$_{42}$H$_{41}$N$_5$O$_7$S (M.W. 759.9) calc.: C, 66.39; H, 5.44; N, 9.22; S, 4.22; found: 66.49; 5.55; 9.25; 4.29.

d) 2-{[(Dimethylamino)-methylene]-amino}-7-deaza-2',3'-dideoxy-5'-O-(4,4'-dimethoxytriphenylmethyl)-9-β-D-ribofuranosylpurine-6-one 500 mg. (0.7 mMole) of the compound from 2c), dissolved in 20 ml. freshly distilled toluene, are mixed with 25 mg. (0.15 mMole) 2,2'-azo-bis-(2-methylpropionic acid nitrile) and 500 μl. (1.9 mMole) tributyl tin hydride and stirred for 16 hours at 80° C. under an atmosphere of argon. Subsequently, the reaction mixture is evaporated under oil pump vacuum and the residue chromatographed on silica gel 60 H (column 20×4 cm., dichloromethane/acetone 9:1 v/v, chloroform/acetone 7:3 v/v, chloroform/acetone 6:4 v/v). The residue obtained by evaporation of the main fraction is dissolved in a little dichloromethane and precipitated out by dropping into n-hexane/diethyl ether to give 320 mg. (80% of theory) of the desired colourless, amorphous compound. TLC (silica gel, methylene chloride/methanol 95:5 v/v): $R_f$=0.3.

UV (methanol): $\lambda_{max.}$=236, 277 (shoulder), 284, 312 nm ($\epsilon$=37200, 12000, 13500, 18000).

$^1$H-NMR ([D$_6$]DMSO): δ=2.02 (m, 3'-H), 2.20, 2.33 (m, 2'-H$_a$ and 2'-H$_b$), 3.02, 3.13 (s, 2 CH$_3$), 3.08 (m, 5'-H), 4.17 (m, 4'-H), 6.31 (d, 6-H, J=3.5 Hz), 6.38 (m, 1'-H), 6.92 (d, 5-H, J=3.5 Hz), 8.61 (s, CH=N), 11.03 (s, NH).

Analysis for C$_{35}$H$_{37}$N$_5$O$_7$ (M.W. 607.7) calc.: C, 69.18; H, 6.14; N, 11.52; found: 69.23; 6.24; 11.61.

e) 2-{[(Dimethylamino)-methylene]-amino}-7-deaza-2',3'-dideoxy-9-β-D-ribofuranosylpurine-6-one 130 mg. (0.21 mMole) of the compound from 2d) are dissolved in 80% acetic acid and stirred for 15 minutes at ambient temperature. Subsequently, the acetic acid is evaporated off under oil pump vacuum and the residue is chromatographed on silica gel 60 H (column 20×2 cm., dichloromethane/methanol 95:5 v/v). The residue obtained by evaporation of the main fraction is foamed up by repeated evaporation with acetone to give 43 mg. (67% of theory) of the desired colourless, amorphous compound. TLC (silica gel, dichloromethane/methanol 9:1 v/v): $R_f$=0.5.

UV (methanol): $\lambda_{max.}$=239, 282 (shoulder), 311 nm ($\epsilon$=17400, 10500, 16900).

$^1$H-NMR ([D$_6$]DMSO): δ=2.06, 2.32 (m, 2'-H and 3'-H), 3.01, 3.14 (s, 2 CH$_3$O), 3.51 (m, 5'-H), 4.00 (m, 4'-H), 4.87 (t, 5'-OH), 6.33 (m, 1'-H and 6-H, J=3.3 Hz), 7.05 (d, 5-H, J=3.3 Hz), 8.59 (s, CH=N), 11.02 (s, NH).

Analysis for C$_{14}$H$_{19}$N$_5$O$_3$ (M.W.305.3) calc.: C, 55.07; H, 6.27; N, 22.94; found: 55.23; 6.41; 22.75.

EXAMPLE 3

2-Amino-6-methoxy-7-deaza-2',3'-dideoxy-9-β-D-ribofuranosylpurine a) 2-Amino-6-methoxy-7-deaza-2'-deoxy-9-β-D-ribofuranosylpurine 543 mg. (10 mMole) finely powdered potassium hydroxide and 68 mg; (0.2 mMole) tetrabutylammonium hydrogen sulphate in 30 ml. anhydrous dichloromethane are stirred for 15 minutes at ambient temperature under an atmosphere of nitrogen. Subsequently, the reaction mixture is mixed with 330 mg. (2 mmole) 2-amino-6-methoxy-7-deazapurine (2-amino-4-methoxy-7H-pyrrolo[2,3-d]-pyrimidine) and stirred for a further 30 minutes. After the addition of 884 mg. (2.2 mMole) 2-desoxy-3,5-di-0-p-toluoyl-β-D-erythro-pentofuranosyl chloride, stirring is continued for a further 3 minutes. Insoluble components are filtered off with suction, washed with a little dichloromethane and the filtrate concentrated to about 10 ml. After mixing with 3 ml. 1M sodium methoxide in methanol, stirring is continued for 3 hours at ambient temperature. After neutralisation with acetic acid, the solvent is stripped off, the residue is taken up in hot water, filtered and the filtrate chromatographed on an exchanger column of Dowex (1×2 OH form, 30×3 cm.) (water/methanol 9:1 v/v). After stripping off the solvent and recrystallising from water, from the main zone there are obtained 260 mg. (63% of theory) of colourless crystals; m.p. 152–154° C. TLC (silica gel, dichloromethane/methanol 9:1 v/v): $R_f$=0.7.

UV (methanol): $\lambda_{max.}$=225, 259, 285 ($\epsilon$=24900, 3600, 7600

$^1$H-NMR ([D$_6$]): δ=6.27 (1H, d, J=3.7 Hz), 6.42 (1H, dd, $J_{1',2'a}$=8.4 Hz, $J_{1',2'b}$=5.9 Hz), 7.10 (1H, d, J=3.7 Hz) ppm.

$^{13}$C-NMR ([D$_6$]DMSO): δ=52.49 (OCH$_3$), 82.37 (C-1'), 98.85 (C-5), 119.45 (C-6) ppm.

b) The compound 2-amino-6-methoxy-7-deaza-2'-deoxy-9-β-D-ribofuranosylpurine obtained according to a) is deoxygenated in the manner described in Example 1c) to give 2-amino-6-methoxy-deaza-2',3'-dideoxy-9-β-D-ribofuranosylpurine

EXAMPLE 4

2-Amino-6-chloro-7-deaza-2',3'-dideoxy-9-β-D-ribofuranosylpurine a) The compound is prepared, after acetylation of 2-amino-7-deaza-2',3'-dideoxy-9-β-D-ribofuranosylpurine-6-one (prepared according to Example 1d) by halogenation according to the method described in Liebigs Ann. Chem., 1987, 15–19.

b) The resulting crude mixture is, for the removal of the acetyl protective group, left to stand for 3 hours in methanolic ammonia solution at ambient temperature, then evaporated to dryness and finally chromatographed on silica gel with the elution agent chloroform/methanol. After combining the main fractions and evaporating, the residue obtained is crystallised from water.

UV (methanol): $\lambda_{max.}$=235, 258, 316 ($\epsilon$=27800, 4300, 5800).

Analysis for C$_{11}$H$_{13}$N$_4$O$_2$Cl (M.W. 268.7) calc.: C, 49.1; H, 4.8; N, 20.8; Cl, 13.0; found: 49.3; 4.85; 20.7; 13.1.

EXAMPLE 5

2-Amino-7-deaza-2',3'-dideoxy-9-β-D-ribofuranosylpurine 268 mg. (1 mMole) 2-amino-6-chloro-7-deaza-2',3'-dideoxy-9-β-D-ribofuranosylpurine are dissolved in 25 ml. 70% aqueous methanol, added to a suspension of 30 mg. prehydrogenated Pd/C (10) in 25 ml. 70% aqueous methanol and hydrogenated until the take up of hydrogen is complete. The solvent is stripped off and the residue is crystallised from methanol. Yield 180 mg. (77% of theory).

Analysis for C$_{11}$H$_{14}$N$_4$O$_2$ (M.W. 234.3) calc.: C, 56.4; H, 6.0; N, 23.9; found: 56.3; 6.0; 23.7.

UV (methanol): $\lambda_{max.}$=234, 256, 314 nm ($\epsilon$=30600, 4100, 5200).

EXAMPLE 6

2-Amino-6-mercapto-7-deaza-2',3'-dideoxy-9-β-D-ribofuranosylpurine 536 mg. (2 mMole) 2-amino-6-chloro-7-deaza-2',3'-dideoxy-9-β-D-ribofuranosylpurine and 1.5 g. (20 mMole) thiourea are suspended in 30 ml. ethanol and heated under reflux for about 15 hours. Thereafter, the solvent is distilled off, the residue is taken up in about 25 ml. methanol and then chromatographed on silica gel 60 H (column 20×3 cm., dichloromethane/methanol 9:1 v/v). By evaporation of the main fraction and crystallisation from methanol/water, there are obtained 230 mg. (43% of theory) of the thio compound.

Analysis for C$_{11}$H$_{14}$N$_4$O$_2$S (M.W. 266.3) calc.: C, 49.6; H, 5.3; N, 21.0; found: 49.4; 5.4; 21.1.

UV (methanol): $\lambda_{max.}$=235, 271, 345 nm ($\epsilon$=176000, 11700, 18700).

$^1$H-NMR ([D$_6$]DMSO): δ=1.9 (m, 3'-H), 2.1 (m, 2'-H$_b$), 2.34 (m, 2'-H$_a$), 3.50 (m, 5'-H), 3.97 (m, 4'-H), 4.86 (t, 5'-OH), 6.12 (m, 1'-H), 6.24 (m, NH$_2$ and 8-H), 6.92 (d, 7-H), 11.1 (s, NH).

EXAMPLE 7

2,6-Diamino-7-deaza-2',3'-dideoxy-9-β-D-ribofuranosylpurine 268 mg. (1 mMole) 2-amino-6-chloro-7-deaza-2',3'-dideoxy-9-β-D-ribofuranosylpurine are mixed with 40 ml. aqueous concentrated ammonia solution and heated for 60 hours at 65° C. on a waterbath in a tightly closed vessel. After evaporation of the solvent, the residue is chromatographed on a silica gel column, first with dichloromethane/methanol (9:1 v/v) (starting material) and then with chloroform/methanol (4:1 v/v). After crystallisation from water, there are obtained 120 mg. (48% of theory) of the desired diamino compound.

Analysis for C$_{11}$H$_{15}$N$_5$O$_2$ (M.W. 249.3) calc.: C, 53.0; H, 6.0; N, 28.1; found: 53.15; 5.9; 28.2.

UV (methanol): $\lambda_{max.}$=264, 284 nm ($\epsilon$=9800, 8000).

$^1$H-NMR ([D$_6$]DMSO: δ=1.9 (m, 3'-H), 2.1, 2.4 (2 m, 2'-H$_{a,b}$), 3.4 (m, 5'-H), 3.8 (m, 4'-H), 4.8 (t, 5'-OH), 5.6 (s, NH$_2$), 6.2 (dd, 1'-H), 6.3 (d, 7-H), 6.7 (s, NH$_2$), 6.9 (d, 8-H).

EXAMPLE 8

2-Methylthio-6-methoxy-7-deaza-2',3'-dideoxy-9-β-D-ribofuranosylpurine a) 2-Methylthio-6-methoxy-7-desaza-2'-desoxy-9-β-D-ribofuranosylpurine 500 mg. (2.56 mMole) 4-Methoxy-2-methylthio-7H-pyrrolo[2,3-d]pyrimidine and 400 mg. (1.75 mMole) benzyltriethylammonium chloride are dissolved in 20 ml. dichloromethane with 20 ml. of a 5% aqueous solution of sodium hydroxide as counterphase and briefly mixed up in a vibratory mixer. 1.2 g. (3.1 mMole) 2-deoxy-3,5-di-O-(p-toluoyl)-β-D-erythro-pentofuranosyl chloride in a little dichloromethane, is added thereto and the vibratory mixing continued for 30 minutes. The organic phase is separated off and the aqueous phase shaken up with dichloromethane. The combined organic extracts are washed with water and dried with anhydrous sodium sulphate. After filtration, the filtrate is evaporated and the residue dissolved in 100 ml. 1M sodium methanolate in methanol. The solution is stirred for about 12 hours at ambient temperature, then evaporated and the residue is taken up in water and adsorbed on a Dowex 1-X2 ion exchanger column (30×3 cm., OH$^-$ form). Elution with water-methanol (1:1 v/v) gives a main zone. After evaporation of the solvent, the residue is recrystallised from water; yield 321 mg. (40% of theory) of colourless needles; m.p. 118° C. TLC (silica gel; dichloromethane/acetone 8:2 v/v): $R_f$=0.26.

UV (methanol): $\lambda_{max.}$=283, 236 nm ($\epsilon$=13000, 15500).

$^1$H-NMR ([D$_6$]DMSO): δ=2.20 (m, 2'-H), 2.40 (m, 2'-H), 2.56 (s, CH$_3$S), 3.50 (m. 5'-H$_2$), 3.81 (m, 4'-H), 4.01 (s, CH$_3$O), 4.35 (m, 3'-H), 4.90 (t, 5'-OH, J=5 Hz), 5.29 (d, 3'-OH, J=4 Hz), 6.48 (d, 5-H, J=4 Hz), 6.55 (t, 1'-H, J=5 Hz), 7.47 (d, 6-H, J=4 Hz).

Analysis for C$_{13}$H$_{17}$N$_3$O$_4$S (M.W. 311.4) calc.: C, 50.15; H, 5.50; N, 13.50; S, 10.30; found: 50.28; 5.47; 13.56; 10.31.

b) 2-Methylthio-6-methoxy-7-deaza-2',3'-dideoxy-9-β-D-ribofuranosylpurine

This is prepared by deoxygenation of the 2'-deoxy compound obtained according to a) in the manner described in Example 1c).

UV (methanol): $\lambda_{max.}$=283, 236 ($\epsilon$=1300, 15500)

Analysis for C$_{13}$H$_{17}$N$_3$O$_3$S (M.W. 295.4) calc.: C, 52.8; H, 5.75; N, 14.2; found: 52.6; 5.70; 14.2.

EXAMPLE 9

6-Methoxy-7-deaza-2',3'-9-β-D-ribofuranosylpurine a) 6-Methoxy-7-deaza-2'-dideoxy-9-β-D-ribofuranosylpurine The synthesis of this compound takes place in the manner described in Liebigs Ann. Chem., 1985, 1360–1366.
b) The dideoxy derivative can be obtained by deoxygenation of the compound obtained in a) in the manner described in Example 1c).

An alternative way is the desulphurisation of 2-methylthio-6-methoxy-7-deaza-2',3'-dideoxy-9-β-D-ribofuranosylpurine from Example 8, also in the manner described in Liebigs Ann. Chem., 1985, 1360–1366. TLC (dichloromethane/methanol 9:1 v/v): $R_f$=0.8.

UV (methanol): $\lambda_{max.}$=261 nm (log ($\epsilon$)=3.86).

$^1$H-NMR (DMSO-d$_6$): δ=2.04 (m, 3'-H), 2.24 (m, 2'-H$_b$), 2.40 (m, 2'-H$_a$), 3.55 (m, 5'-H), 4.04 (s, OCH$_3$), 4.07 (m, 4'-H), 4.93 (t, J=5.5 Hz, 5'-OH), 6.47 (dd, J=4.4 and 6.8 Hz, 1'-H), 6.55 (d, J=3.7 Hz, 5-H), 7,66 (d, J=3.7 Hz, 6-H), 8.42 (s, 2-H).

Analysis for C$_{12}$H$_{15}$N$_3$O$_3$ (M.W. 249.3) calc.: C, 57.8; H, 6.0; N, 16.8; found: 57.8; 6.05; 16.65.

Another possibility for the preparation of this compound is described in Example 24i).

EXAMPLE 10

7-Deaza-2',3'-dideoxy-9-β-D-ribofuranosylpurine-6-one

The preparation of this compound takes place via the 2'-desoxy compound as described in Liebigs Ann. Chem., 1985, 312–320 and subsequent deoxygenation as described in Example 1c).

UV (methanol): $\lambda_{max.}$=258, 280 (shoulder) ($\epsilon$=9200, 6400).

TLC (dichloromethane/methanol 9:1 v/v): $R_f$=0.5.

$^1$H-NMR (DMSO-d$_6$): δ=2.00 (m, 3'-H), 2.16 (m, 2'-H$_b$), 2.37 (m, 2'-H$_a$), 3.49 (dd, J=4.9 and 11.6 Hz, 5'-H), 3.58 (dd, J=4.2 and 11.6 Hz, 5'-H), 4.05 (m, 4'-H), 6.33 (dd, J=4.2 and 6.9 Hz, 1'-H), 6.50 (d, J=3.5 Hz, 5-H), 7.36 (d, J=3.5 Hz, 6-H), 7.90 (s, 2H).

Analysis for C$_{11}$H$_{13}$N$_3$O$_3$ (M.W. 235.2) calc.: C, 56.1; H, 5.5; N, 17.8; found: 56.0; 5.3; 18.0.

A further possibility for the preparation of this compound is described in Example 24j).

EXAMPLE 11

7-Deaza-2',3'-dideoxy-9-β-D-ribofuranosylpurine-2,6-dione.

The synthesis of this compound takes place via the 2'-desoxy compound as described in Liebigs Ann. Chem., 1985, 312–320 and subsequent deoxygenation as described in Example 1c).

UV (phosphate buffer; pH 7.0): $\lambda_{max.}$=251, 280 nm ($\epsilon$=10500, 7400)

Analysis for C$_{11}$H$_{13}$N$_3$O$_4$ (M.W. 251.4) calc.: C, 52.5; H, 5.2; N, 16.7; found: 52.3; 5.1; 16.5.

EXAMPLE 12

2,6-Dimethoxy-7-deaza-2',3'-dideoxy-9-β-D-ribofuranosylpurine

This derivative is synthesised by phase transfer glycosylation and subsequent deoxygenation as described in Example 1c).

UV (methanol): $\lambda_{max.}$=257, 271 nm ($\epsilon$=7300, 7400)

Analysis for C$_{13}$H$_{17}$N$_3$O$_4$ (M.W. 279.3) calc.: C, 55.85; H, 6.1; N, 15.0; found: 55.7; 6.1; 15.1.

EXAMPLE 13

6-Amino-7-deaza-2',3'-dideoxy-9-β-D-ribofuranosylpurine-2-one

This compound is obtained according to J. Chem. Soc., Perkin Trans. II, 1986, 525–530 by phase transfer glycosylation of 2-methoxy-6-amino-7-deazapurine, subsequent demethylation and finally deoxygenation analogously to Example 1c).

UV (methanol): $\lambda_{max.}$=255, 305 nm ($\epsilon$=7600, 7200)

Analysis for C$_{11}$H$_{14}$N$_4$O$_3$ (M.W. 250.2) calc.: C, 52.7; H, 5.6; N, 22.4; found: 52.75; 5.5; 22.3.

EXAMPLE 14

2-Amino-7-deaza-7-methyl-2',3'-dideoxy-9-β-D-ribofuranosylpurine-6-one

This compound is synthesised via the 2'-dideoxy-nucleoside described in Liebigs Ann. Chem., 1984, 708–721 with subsequent deoxygenation as described in Example 1c).

UV (methanol): $\lambda_{max.}$=224, 264, 285 nm (shoulder) ($\epsilon$=22500, 10500, 6500)

Analysis for C$_{12}$H$_{16}$N$_4$O$_3$ (M.W. 264.3) calc.: C, 54.5; H, 6.05; N, 21.2; found: 54.3; 6.1; 21.1.

EXAMPLE 15

2-Amino-7-desaza-2',3'-didesoxy-3'-azido-9-β-D-ribofuranosylpurin-6-one

This compound is prepared by glycosylation of 2-amino-7-deazapurine-6-one with the azido sugar prepared according to Byatkina/Azhayev (Synthesis, 1984, 961–963).

UV (methanol): $\lambda_{max.}$=261, 281 nm (shoulder) ($\epsilon$=13300, 7800).

Analysis for $C_{11}H_{13}N_7O_3$ (M.W. 291.3) calc.: C, 45.3; H, 4.45; N, 33.65; found: 45.4; 4.3; 33.4.

EXAMPLE 16

3,7-Dideaza-2',3'-dideoxy-3'-azido-9-β-D-ribofuranosylpurine

This compound is prepared by ribosidation of 3,7-didesazapurine with the azido sugar prepared according to Byatkina/Azhayev (Synthesis, 1984, 961–963).

UV (methanol): $\lambda_{max.}$=224, 274 nm.

Analysis for $C_{12}H_{13}N_5O_2$ (M.W. 259.2) calc.: C, 55.55; H, 5.0; N, 27.0; found: 55.4; 5.1; 26.8.

EXAMPLE 17

6-Amino-8-aza-7-deaza-2',3'-dideoxy-9-β-D-ribofuranosylpurine (4-amino-1-(2-desoxy-β-D-erythro-pentofuranosyl)-1H-pyrazolo[3,4-d]pyrimidine)

a) 4-Benzoylamino-1-(2'-deoxy-9-β-D-erythro-pentofuranosyl-5'-O-(4,4'-dimethoxytriphenylmethyl)-1H-pyrazolo[3,4-d]pyrimidine 6-Amino-8-aza-7-deaza-2'-deoxy-β-D-ribofuranosylpurine is prepared in the manner described in Helv. Chim. Acta, 68, 563–570/1985. The benzoylation of the 4-amino group and the subsequent introduction of the dimethoxytrityl protective group is carried out analogously to known methods.

b) 4-Benzoylamino-1-(2'-deoxy-β-D-erythro-pentofuranosyl)-5'-O-(4,4'-dimethoxytriphenylmethyl)-3'-O-phenoxythiocarbonyl-1H-pyrazolo[3,4-d]-pyrimidine 200 mg. (0.3 mMole) of the product of Example 17a) are reacted in 4 ml. acetonitrile with 82 μl. (0.6 mMole) phenyl chlorothiocarbonate at ambient temperature for 16 hours in the presence of 90 mg. (0.75 mMole) 4-(dimethylamino)-pyridine. After chromatographic purification (silica gel, dichloromethane/ethyl acetate 95:5 v/v), there are isolated 150 mg. (63% of theory) of the desired product.

TLC (silica gel, dichloromethane/ethyl acetate, 95:5 v/v: $R_f$=0.4.

$^1$H-NMR ([$D_6$]DMSO): δ=3.26 (m, 5'-H), 3.69 (s, 2×OCH$_3$), 4.45 (m, 4'-H), 5.98 (m, 3'-H), 8.45 (s, 3-H), 8.78 (s, 6-H), 11.72 (s, NH).

c) 4-Benzoylamino-1-(2',3'-dideoxy-9-β-D-glyceropentofuranosyl)-5'-O-(4,4'-dimethoxytriphenylmethyl)-1H-pyrazolo[3,4-d]pyrimidine 200 mg. (0.25 mMole) of the product of Example 17b) are deoxygenated according to Barton's method in 7 ml. toluene with 150 μl. (0.55 mMole) tri-N-butyl stannane at 80° C. under an atmosphere of argon. After chromatography (silica gel, dichloromethane/ethyl acetate 95:5 v/v), there are obtained 120 mg. (75% of theory) of the desired colourless and amorphous product.

TLC (silica gel, dichloromethane/ethyl acetate 95:5 v/v): $R_f$=0.3.

$^1$H-NMR ([$D_6$]DMSO): δ=2.16 (m, 3'-H), 2.49 (m, 2'-H), 2.99 (m, 5'-H), 3.65, 3.68 (2s, 2×OCH$_3$), 4.32 (m, 4'-H), 6.69 (m, 1'-H), 8.41 (s, 3-H), 8.80 (s, 6-H), 11.66 (s, NH).

d) 6-Amino-8-aza-7-deaza-2',3'-dideoxy-9-β-D-ribofuranosylpurine (4-amino-1-(2',3'-didesoxy-β-D-glyceropentofuranosyl)-1H-pyrazolo[3,4-d]pyrimidine)

a) 300 mg. (0.47 mMole) of the product of Example 17c) are treated in 40 ml. ammonia-saturated methanol at 60° C. for 4 hours and then evaporated to dryness. There are obtained 200 mg. (81% of theory) 4-amino-1-(2',3'-dideoxy-β-D-glyceropentofuranosyl)-5'-O-(4,4'-dimethoxy-triphenylmethyl)-1H-pyrazolo[3,4-d]pyrimidine in the form of a colourless foam after chromatography on silica gel (dichloromethane/acetone 7:3 v/v).

TLC (silica gel, dichloromethane/acetone 8:2 v/v): $R_f$=0.25.

$^1$H-NMR ([$D_6$]DMSO): δ=2.16 (m, 3'-H), 2.45 (m, 2'-H), 2.99 (m, 5'-H), 3.69, 3.70 (2s, 2×OCH$_3$), 4.25 (m, 4'-H), 6.52 (m, 1'-H), 7.74 (s, NH$_2$), 8.06 (s, 3-H), 8.24 (s, 6-H).

b) 110 mg. (0.2 mMole) of the above product are stirred for 20 minutes at ambient temperature in 10 ml. 80% acetic acid. After chromatography (silica gel, dichloromethane/methanol 9:1 v/v), there is obtained the desired product in crystalline form. Subsequent re-crystallisation from isopropanol/cyclohexane gives 40 mg. (85% of theory) of the desired product as a colourless solid.

UV (methanol): $\lambda_{max.}$=260, 275 nm ($\epsilon$=9000, 10200).

Analysis for $C_{10}H_{13}H_5O_2$ (M.W. 235.25) calc.: C, 51.06; H, 5.57; N, 29.77; found: 50.96; 5.65; 29.80.

$^{13}$C-NMR ([$D_6$]DMSO): δ=133 (C-8), 100.3 (C-5), 158.1 (C-6), 156.1 (C-2), 153.6 (C-4), 84.4 (C-1'), 30.4 (C-2'), 27.4 (C-3'), 81.7 (C-4'), 64.3 (C-5').

TLC (silica gel, dichloromethane/methanol 9:1 v/v): $R_f$=0.4.

UV (methanol): $\lambda_{max.}$=260, 275 nm ($\epsilon$=9000, 10200 ).

$^1$H-NMR ([$D_6$]DMSO): δ=2.11 (m, 3'-H), 2.40 (m, 2'-H), 3.36 (m, 1'-H), 4.08 (m, 4'-H), 4.75 (m, 5'-OH), 6.45 (m, 1'-H), 7.75 (s, NH$_2$), 8.14 (s, 3-H), 8.18 (s, 6-H).

EXAMPLE 18 a) 4,6-Dichloro-1-(2'-deoxy-3',5'-di-O-p-toluoyl-β-D-erythro-pentofuranosyl)-1H-pyrrolo[3,2-c]pyridine A solution of 300 mg. (1.6 mMole) 4,6-dichloro-1H-pyrrolo[3,2-c]pyridine in 75 ml. dry acetonitrile, which contains 450 mg. (8.0 mMole) potassium hydroxide and 30 mg. (0.1 mMole) tris-[2-(2-methoxyethoxy)-ethyl]-amine, is stirred at ambient temperature for 30 minutes under an atmosphere of nitrogen. While stirring, 625 mg. (1.6 mMole) α-chloro-2-desoxy-3,5-di-O-p-toluoyl-D-erythro-pentofuranose are added thereto and stirring continued for 15 minutes. Insoluble material is then filtered off and the filtrate is evaporated in a vacuum. The oily residue is chromatographed on silica gel (column 17×4 cm., elution agent dichloromethane/ethyl acetate 97:3 v/v). There are obtained 762 mg. (90% of theory) of the colourless, amorphous product.

$^1$H-NMR (Me$_2$SO-d$_6$): δ=2.37 and 2.41 (2s, 2 CH$_3$), 2.77 (m, H-2's), 2.94 (m, H-2'), 4.57 (m, H-4', H-5'), 5.68 (m, H-3'), 6.66 (pt, H-1'), 6.71 (d, J=3.5 Hz, H-3), 8.00 (s, H-7).

$^{13}$C-NMR (Me$_2$SO-d$_6$): δ=36.8 (C-2'), 64.2 (C-5'), 74.9 (C-3'), 81.7 (C-1'), 85.6 (C-4'), 102.0 (C-3), 106.1 (C-7), 123.1 (C-3a), 129.7 (C-2), 140.0 (C-6), 140.6 (C-4), 142.4 (C-7a).

b) 4,6-Dichloro-1-(2'-deoxy-β-D-erythro-pentofuranosyl)-1H-pyrrolo[3,2-c]pyridine 500 mg. (0.93 mMole) of the compound of Example 18a) are dissolved in 30 ml. methanolic ammonia and stirred for 12 hours at 50° C. The solution is evaporated to dryness, the solid residue is adsorbed in silica gel 60 H (2 g.) and applied to a silica gel column (14×4 cm., elution agent chloroform/methanol 9:1 v/v). From the main fraction there is isolated the desired product in the form of a colourless oil which crystallises from aqueous ethanol in the form of colourless needles.

Yield 101 mg. (72% of theory); m.p. 180° C.

$^1$H-NMR (Me$_2$SO-d$_6$): δ=2.28 (m, H-2's), 2.43 (m, H-2'a), 3.56 (m, H-5'), 3.85 (m, H-4'), 4.38 (m, H-3'), 5.02 (t, J=5.2 Hz, 5'-OH), 5.34 (d, J=4.1 Hz, 3'-OH), 6.42 (pt, H-1'), 6.67 (d, J=3.4 Hz, H-3), 7.89 (d, J=3.4 Hz, H-2), 7.96 (s, H-7).

$^{13}$C-NMR (Me$_2$SO-d$_6$): δ=40.6 (C-2'), 61.5 (C-5'), 70.5 (C-3'), 85.5 (C-1'), 87.6 (C-4'), 101.3 (C-3), 106.1 (C-7), 123.1 (C-3a), 129.2 (C-2), 139.7 (C-6), 140.4 (C-4), 142.0 (C-7a).

c) 4-Amino-6-chloro-1-(2'-deoxy-β-D-erythro-pentofuranosyl)-1H-pyrrolo[3,2-c]pyridine 460 mg. (1.52 mMole) of the compound of Example 18b) are dissolved in 6 ml. dry hydrazine and heated to 80° C. for 60 minutes. The hydrazine is removed under a vacuum and the oily residue evaporated twice with, in each case, 10 ml. ethanol. The residue is dissolved in 40 ml. aqueous ethanol and then 2 g. Raney nickel are added thereto and the mixture heated to the boil for 2 hours, while stirring. The catalyst is filtered off and thoroughly washed with hot aqueous ethanol. The filtrate is evaporated to dryness, the residue is dissolved in methanol, adsorbed on 2 g. silica gel and the solvent removed under a vacuum. This silica gel is suspended in chloroform/methanol (9:1 v/v) and applied to a silica gel column (6×3 cm.). Elution with chloroform/methanol (9:1 v/v) gives a colourless syrup from which, by crystallisation from methanol, the product can be obtained in the form of small, colourless crystals; m.p. 232° C. Yield: 207 g. (48% of theory).

TLC (chloroform/methanol 9:1 v/v): R$_f$=0.2.

UV (methanol): λ$_{max.}$=277 nm (ε=14800 ), 285 nm (ε=13800).

$^1$H-NMR (Me$_2$SO-d$_6$): δ=2.20 (m, H-2'm), 2.40 (m, H-2'a), 3.51 (m, H-5'), 3.78 (m, H-4'), 4.32 (m, H-3'), 4.89 (t, J=5 Hz, 5'-OH), 5.26 (d, J=4 Hz, 3'-OH), 6.19 (pt, H-1'), 6.55 (s, NH$_2$), 6.64 (d, J=3 Hz, H-3), 6.83 (s, H-7), 7.36 (d, J=3 Hz, H-2).

$^{13}$C-NMR (Me$_2$SO-d$_6$): δ=40 (C-2'), 61.8 (C-5'), 70.6 (C-3'), 84.7 (C-1'), 87.2 (C-4'), 95.1 (C-7), 101.6 (C-3), 109.6 (C-3a), 123.5 (C-2), 141.0 (C-6), 141.4 (C-7a), 152.9 (C-4).

Analysis for C$_{12}$H$_{14}$ClN$_3$O$_3$ calc.: C, 50.80; H, 4.97; N, 14.81; Cl, 12.50; found: 50.91; 5.05; 14.75; 12.53.

d) 4-Amino-1-(2'-deoxy-β-D-erythro-pentofuranosyl)-1H-pyrrolo[3,2-c]pyridine A solution of 200 mg. (0.7 mMole) of the compound from Example 18c) in 30 ml. methanol, which contains 0.4 ml. of ammonia-saturated methanol, is hydrogenated in the presence of palladium/charcoal (50 mg., 10% Pd) at ambient temperature for 30 hours. The catalyst is filtered off and the solvent removed in a vacuum. Purification by flash chromatography (column 4×4 cm., elution agent chloroform/methanol/triethylamine 7:3:2 v/v/v) and crystallisation from methanol gives 70 mg. (40% of theory) of the desired product in the form of colourless crystals; m.p. 205° C.

TLC (elution agent chloroform/methanol/triethylamine 7:3:2 v/v/v): R$_f$=0.4.

UV (methanol): λ$_{max.}$=271 nm (ε=12800).

$^1$H-NMR (Me$_2$SO-d$_6$): δ=2.20 (m, H-2'b), 2.42 (m, H-2'a), 3.51 (m, H-5'), 3.80 (m, H-4'), 4.32 (m, H-3'), 4.91 (m, 5'-OH), 5.32 (m, 3'-OH), 6.08 (s, NH$_2$), 6.23 (pt, H-1'), 6.65 (d, J=3 Hz, H-3), 6.75 (d, J=6 Hz, H-7), 7.35 (d, J=3 Hz, H-2), 7.55 (d, J=6 Hz, H-6).

$^{13}$C-NMR (Me$_2$SO-d$_6$): δ=39.8 (C-2'), 62.0 (C-5'), 70.8 (C-3'), 84.5 (C-1'), 87.1 (C-4'), 96.9 (C-7), 101.5 (C-3), 110.7 (C-3a), 122.5 (C-2), 139.7 (C-6), 140.0 (C-7a), 153.7 (C-4).

Analysis for C$_{12}$H$_{15}$N$_3$O$_3$ calc.: C, 57.82; H, 6.07; N, 16.86; found: 57.97; 6.12; 16.74.

EXAMPLE 19 a) 6-Chloro-1-(2'-deoxy-β-D-erythro-pentofuranosyl)-1H-pyrrolo[3,2-c]pyridin-4-one A solution of 400 mg. (1.32 mMole) of the compound of Example 18b) is heated to the boil for 30 hours in 2N aqueous sodium hydroxide solution with a small amount of 1,4-dioxan. The reaction mixture is neutralised with 2N hydrochloric acid, filtered and then applied to an Amberlite XAD 4 column (17×2 cm.). Inorganic salts are removed by washing with water and then the product is eluted with methanol. Crystallisation from water gives 158 mg. (42% of theory) of colourless crystals; m.p. 242–243° C.

TLC (chloroform/methanol 8:2 v/v): R$_f$=0.5.

UV (methanol): λ$_{max.}$=270 nm (ε=11100), 292 nm (ε=9300).

$^1$H-NMR (Me$_2$SO-d$_6$): δ=2.22 (m, H-2'b), 2.38 (m, H-2'a), 3.53 (m, H-5'), 3.80 (m, H-4'), 4.33 (m, H-3'), 4.96 (m, 5'-OH), 5.29 (m, 3'-OH), 6.22 (pt, H-1'), 6.54 (d, J=3.3 Hz, H-3), 6.96 (s, H-7), 7.38 (d, J=3.3 Hz, H-2), 11.81 (br. NH).

$^{13}$C-NMR (Me$_2$SO-d$_6$): δ=40.5 (C-2'), 61.7 (C-5'), 70.6 (C-3'), 85.0 (C-1'), 87.4 (C-4'), 94.9 (C-7), 104.1 (C-3), 114.0 (C-3a), 123.2 (C-2), 129.1 (C-6), 139.2 (C-7a), 158.7 (C-4).

Analysis for C$_{12}$H$_{13}$ClN$_2$O$_4$ calc.: C, 50.63; H, 4.60; N, 9.84; Cl, 12.45; found: 50.79; 4.74; 9.80; 12.69.

b) 1-(2'-Deoxy-β-D-erythro-pentofuranosyl)-1H-pyrrolo[3,2-c]pyridin-4-one

A solution of 100 mg. (0.35 mMole) of the compound of Example 19a) in 15 ml. methanol is mixed with 0.5 ml. 25% aqueous ammonia solution and hydrogenated in the presence of palladium/animal charcoal (10% Pd, 15 mg.) for 3 hours at ambient temperature. The catalyst is filtered off and the filtrate evaporated to dryness. The solid residue is crystallised from water. There are obtained 51 mg. (58% of theory) of the desired product; m.p. 147–148° C.

TLC (elution agent chloroform/methanol 8:2 v/v): R$_f$=0.3.

UV (methanol): λ$_{max.}$=264 nm (ε=11700), 282 nm (sh, ε=8000), 295 nm (sh, ε=5100).

$^1$H-NMR (Me$_2$SO-d$_6$): δ=2.22 (m, H-2's), 2.40 (m, H-2's), 3.52 (m, H-5'), 3.81 (m, H-4'), 4.32 (m, H-3'), 4.93 (t, J=5.4 Hz, 5'-OH), 5.32 (d, H=4.3 Hz, 3'-OH), 6.21 (pt, H-1'), 6.54 (d, J=3 Hz, H-3), 6.62 (d, J=7 Hz, H-7), 7.03 (d, J=7 Hz, H-6), 7.34 (d, J=3 Hz, H-2), 10.87 (br NH).

$^{13}$C-NMR (Me$_2$SO-d$_6$): δ=40 (C-2', superimposed by solvent signals), 61.8 (C-5'), 70.7 (C-3'), 84.8 (C-1'), 87.4 (C-4'), 93.8 (C-7), 104.6 (C-3), 115.9 (C-3a), 122.0 (C-2), 127.8 (C-6), 139.0 (C-7a), 159.6 (C-4).

Analysis for C$_{13}$H$_{14}$N$_2$O$_4$ calc.: C, 59.08; H, 6.10; N, 10.60; found: 59.09; 6.07; 10.65.

EXAMPLE 20 a) 1-(2'-Deoxy-β-D-erythro-pentofuranosyl)-4,6-dichloro-5'-0-(4,4'-dimethoxytrityl)-1H-pyrrolo-[3,2-c]pyridine 500 mg. (1.65 mMole) of the compound of Example 18b) are evaporated to dryness with 10 ml. pyridine. The material is dissolved in 10 ml. dry pyridine and 0.7 ml. (4.1 mMole) of Hünig's bases, as well as 690 mg. (2.0 mMole) 4,4'-dimethoxytrityl chloride, added thereto. The solution is stirred for 1 hour at ambient temperature. After the addition of 75 ml. of 5% aqueous sodium bicarbonate solution, it is extracted twice with, in each case, 75 ml. dichloromethane. The combined organic phases are dried over anhydrous sodium sulphate. The sodium sulphate is filtered off and the filtrate evaporated. The residue is applied to a silica gel column (30×3 cm.; elution agent dichloromethane/acetone 99:1 v/v). The product is obtained from the main fraction in the form of a yellowish amorphous mass. The product is dissolved in diethyl ether and precipitated out with n-hexane. Yield 740 mg. (74% of theory).

$^1$H-NMR (Me$_2$SO-d$_6$): δ=2.39 (m, H-2'b), 2.64 (m, H-2'a), 3.09 (m, H-5'), 3.72 (s, 2 OCH$_3$), 3.96 (m, H-4'), 4.42 (m, H-3'), 5.41 (d, J=4.8 Hz, 3'-OH), 6.47 (pt, H-1'), 6.65 (d, J=3.5 Hz, H-3), 6.76–7.27 (aromat. H), 7.76 (d, J=3.5 Hz, H-2), 7.89 (s, H-7).

$^{13}$C-NMR (Me$_2$SO-d$_6$): δ40 (C-2' superimposed by solvent signals), 55.1 (2 OCH$_3$), 63.6 (C-5'), 70.05 (C-3'), 85.0 85.5. 85.5 (C-1', C-4', OCDMT), 101.3 (C-3), 106.2 (C-7), 123.2 (C-3a), 129.1 (C-2), 139.8 (C-6), 140.5 (C-4), 142.3 (C-7a).

Analysis for C$_{33}$H$_{30}$Cl$_2$N$_2$O$_5$ calc.: C, 65.46; H, 4.99; Cl, 11.71; N, 4.63; found: 65.47; 5.09; 11.78; 4.56.

b) 1-(2'-Deoxy-β-D-erythro-pentofuranosyl)-4,6-dichloro-5'-0-(4,4'-dimethoxytrityl)-3'-0-phenoxythiocarbonyl-1H-pyrrolo[3,2-c]pyridine 300 mg. (0.5 mMole) of the compound of Example 20a) are dissolved in 11 ml. dry acetonitrile and 350 mg. (2.8 mMole) 4-dimethylaminopyridine and 150 μl. (1.1 mMole) phenyl chlorothiocarbonate added thereto and the solution is stirred for 16 hours at ambient temperature. The reaction mixture is subsequently evaporated to dryness in a vacuum. The residue is chromatographed on silica gel (elution agent dichloromethane). The colourless product is isolated from the main fraction. Yield 310 mg. (84% of theory).

$^1$H-NMR (Me$_2$SO-d$_6$): δ=2.92 (m, H-2'a,b), 3.35 (m, H-5'), 3.72 (s, 2 OCH$_3$), 4.43 (m, H-4'), 5.89 (m, H-3'), 6.61 (pt, H-1'), 6.71 (d, J=3.5 Hz, H-3), 6.81–7.52 (aromat. H), 7.76 (d, J=3.5 Hz, H-2), 8.01 (s, H-7).

$^{13}$C-NMR (Me$_2$SO-d$_6$): δ=37.0 (C-2'), 55.1 (2 OCH$_3$), 63.8 (C-5'), 83.0, 84.2, 85.6, 86.0 (C-1', C-3', C-4', OCDMT), 101.8 (C-3), 106.3 (C-7), 123.1 (C-3a), 128.9 (C-2), 140.1 (C-6), 140.6 (C-4), 142.4 (C-7a), 193.8 (C=S).

Analysis for C$_{40}$H$_{34}$Cl$_2$N$_2$O$_6$S calc.: C, 64.78; H, 4.62; Cl, 9.55; N, 3.77; S, 4.32; found: 64.66; 4.59; 9.65; 3.70; 4.40.

c) 4,6-Dichloro-1-(2',3'-dideoxy-β-D-glyceropentofuranosyl)-5'-0-(4,4'-dimethoxytrityl)-1H-pyrrolo-[3,2-c]pyridine 170 mg. (0.23 mMole) of the compound of Example 20 b) and 15 mg. (0.1 mMole) 2,2'-azo-bis-(2-methyl)-propionitrile are dissolved in 10 ml. dry toluene under an atmosphere of argon. 140 μl. (0.51 mMole) tri-n-butyl stannane are added thereto, while stirring, and the reaction mixture is then further stirred for 3 hours at 80° C. The solvent is removed under a vacuum and the residue chromatographed on silica gel (elution agent dichloromethane). From the main fraction are isolated 115 mg. (85% of theory) of the desired product.

$^1$H-NMR (Me$_2$SO-d$_6$): δ=2.05 (H-3'), 2.50 (H-2', superimposed by signals of the solvent), 2.90–3.15 (m, H-5'), 4.25 (m, H-4'), 6.38 (m, H-1'), 6.63 (d, J=3.4 Hz, H-3), 6.69–7.30 (aromat. H), 7.79 (d, J=3.4 Hz, H-2), 7.89 (s, H-7).

d) 2,6-Dichloro-3,7-dideaza-2',3'-dideoxy-9-β-D-ribofuranosylpurine

The dimethoxytrityl protective group is removed from the compound of Example 20c) analogously to Example 24f).

e) 6-Amino-3,7-dideaza-2',3'-dideoxy-9-β-D-ribofuranosylpurine

The compound of Example 20d) is treated with hydrazine and subsequently reduced with Raney nickel in the manner described in Example 18c). There is thus obtained the compound described in Example 1D).

f) 3,7-Dideaza-2',3'-dideoxy-9-β-D-ribofuranosylpurine

The compound of Example 20d) is hydrogenated in the presence of palladium/animal charcoal/hydrogen analogously to Example 24g). There is obtained the compound already described in Example 1A).

g) 3,7-Dideaza-2',3'-dideoxy-9-β-D-ribofuranosylpurine-6-one

The compound of Example 20d) is treated with an aqueous solution of sodium hydroxide in the manner described in Example 19a) and subsequently hydrogenated in the manner described in Example 19b). There is thus obtained the compound already described in Example 1E).

EXAMPLE 21

2-Amino-(2',3'-dideoxy-β-D-glyceropentofuranosyl)-1H-pyrazolo[3,4-d]pyrimidin-4-one This compound is prepared analogously to the method described in Example 17 via 2-amino-(2'-deox-9-β-D-ribofuranosyl)-1H-pyrazolo[3,4-d]pyrimidin-4-one and Barton deoxygenation of 2-amino-(2'-deoxy-3'-0-methoxythiocarbonyl-5'-toluoylribofuranosyl)-1H-pyrazolo-[3,4-d]pyrimidin-4-one; m.p. 221° C.

Analysis for C$_{10}$H$_{13}$H$_5$O$_3$ (M.W. 251.25) calc.: C, 47.81; H, 5.22; N, 27.88; found: 48.01; 5.30; 27.83.

$^{13}$C-NMR (DMSO-d$_6$): δ=135.1 (C-3), 99.7 (C-3a), 157.9 (C-4), 155.3 (C-6), 154.5 (C-7a), 83.8 (C-1'), 30.3 (C-2'), 27.3 (C-3'), 81.6 (C-4'), 64.3 (C-5').

$^1$H-NMR: δ=6.19 (dd, 1'-H, J=6.9, 3.5 Hz), 2.06 (m, 3'-H).

EXAMPLE 22

3,7-Dideaza-2'-deoxy-9-β-D-ribofuranosylpurine (2'-deoxy-3,7-didesazanebularin)

The compound of Example 18b) is hydrogenated in the presence of palladium/animal charcoal (10% Pd) in ammoniacal methanol. After filtering off the catalyst and evaporating the filtrate in a vacuum, the product is purified from inorganic salts by chromatography on Amberlite XAD (methanol/water), as well as by crystallisation from water; m.p. 175–176° C.

UV (0.1 m aqueous hydrochloric acid): $\lambda_{max.}$=224, 274 nm $^{13}$C-NMR ([D$_6$]DMSO): δ=126.9 (C-2), 101.7 (C-3), 125.5 (C-3a), 143.3 (C-4), 140.6 (C-6), 105.9 (C-7), 139.2 (C-7a), 84.6 (C-1'), 70.8 (C-3'), 87.8 (C-4'), 61.9 (C-5').

$^1$H-NMR (DMSO-d$_6$): δ=2.23 (m, 2'-Hb), 2.29 (m, 2'-Ha), 3.55 (m, 5'-H$_2$), 3.85 (m, 4'-H), 4.38 (m, 3'-H), 4.99 (5'-OH), 5.37 (3'-OH), 6.42 (pt, 1'-H), 6.66 (d, J=3 Hz, 3H), 7.62 (d, J=6 Hz, 7-H), 7.71 (d, J=3 Hz, 2-H), 8.21 (d, J=6 Hz, 6-H), 8.23 (s, 4-H).

Analysis for $C_{12}H_{14}N_2O_3$ calc.: C, 61.53; H, 6.02; N, 11.96; found: 61.55; 6.12; 12.02.

EXAMPLE 23 a) 2-Chloro-6-methoxy-3,7-dideaza-2'-deoxy-9-β-D-ribofuranosylpurine

The compound of Example 18b) is heated for 40 hours in 1N methanolic sodium methanolate solution. The reaction product is purified on Amberlite XAD by hydrophobic chromatography (methanol/water).

UV (methanol): $\lambda_{max.}$=271, 280 nm.

Analysis for $C_{13}H_{15}ClN_2O_4$ calc.: C, 52.27; H, 5.06; Cl, 11.87; N, 9.38;found: 52.24; 5.14; 12.05; 9.46.

b) 2-Chloro-3,7-dideaza-2'-deoxy-9-β-D-ribofuranosylpurine-6-one.

Heating the compound of Example 18b) for 30 hours in 2N aqueous sodium hydroxide solution/1,4-dioxan gives the desired compound.

UV (methanol): $\lambda_{max.}$=262 nm

Analysis for $C_{13}H_{16}N_2O_4$ calc.: C, 59.08; H, 6.10; N, 10.60; found: 59.09; 6.07; 10.65.

$^1$H-NMR ([D$_6$]DMSO): δ=2.22 (m, 2'-H$_b$), 2.38 (m, 2'-H$_a$), 3.53 (m, 5'-H$_2$), 3.80 (m, 4'-H), 4.33 (m, 3'-H), 4.96 (5'-OH), 5.29 (3'-OH), 6.22 (pt, 1'-H), 6.54 (d, J=3 Hz, 3-H), 6.96 (s, 7-H), 7.38 (d, J=3 Hz, 2-H), 11.81 (NH).

EXAMPLE 24 a) 4-Chloro-7-(2'-deoxy-3,5-di-0-(p-toluoyl)-β-D-erythro-pentofuranosyl)-7H-pyrrolo[2,3-d]pyrimidine.

1 g. (17.8 mMole) powdered potassium hydroxide is introduced at ambient temperature into 60 ml. dry acetonitrile. 100 μl (0.31 mMole) tris-[2-(2-methoxy-ethoxy)-ethyl]-amine are added thereto, while stirring. After 5 minutes, 1.23 g. (8.01 mMole) 4-chloro-7H-pyrrolo[2,3-d] pyrimidine are dissolved in the reaction mixture which is stirred for a further 5 minutes. α-Chloro-2-deoxy-3,5-di-0-p-toluoyl-β-D-erythro-pentofuranose is then added thereto. After stirring for 15 minutes, insoluble material is removed by filtration. The filtrate is evaporated to dryness in a vacuum and the residue chromatographed on a silica gel column (5×7 cm., chloroform). After evaporation of the eluate in a vacuum there are obtained 3.26 g. (81% of theory) of product which crystallises from ethanol in the form of colourless needles; m.p. 120° C.

Further variants of the process of preparation:

(I) Solid-liquid glycosilation in the absence of a catalyst. The reaction is carried out as described above but without the use of a catalyst. After working up, there are obtained 2.82 g. (70% of theory) of the product.

(II) By liquid-liquid phase transfer glycosilation: 500 mg. (3.26 mMole) 4-chloro-7H-pyrrolo[2,3-d]-pyrimidine are dissolved in 20 ml. dichloromethane. 9 ml. of 50% aqueous sodium hydroxide solution are added thereto. After the addition of 10 mg. (0.03 mMole) tetrabutylammonium hydrogen sulphate, the solution is stirred for 1 minute with a vibratory mixer. Subsequently, 1.4 g. (3.61 mMole) of the above-described halogenose is added thereto and mixing continued for a further 3 minutes, whereafter the phases are separated. The aqueous phase is extracted twice with, in each case, 25 ml. dichloromethane. The combined organic phases are dried over anhydrous sodium sulphate. The filtrate is evaporated to dryness and the residue is chromatographed on silica gel (column 5×5 cm., chloroform). Isolation of the product from the main fraction and crystallisation from ethanol gives 1.04 g. (63% of theory) of the desired product; m.p. 118° C. TLC (cyclohexane/ethyl acetate 3:2 v/v): $R_f$=0.7.

UV (methanol): $\lambda_{max.}$=240 nm (log ε=4.48).

$1_H$-NMR (DMSO-d$_6$): δ=2.37, 2.40 (s, 2 CH$_3$), 2.77 (m, 2'-H$_b$), 3.18 (m, 2'-Ha), 4.60 (m, 4'-H and 5'-H), 5.77 (m, 3'-H), 6.75 (d, J=3.7 Hz, 5-H), 6.78 (m, 1'-H), 7.34, 7.91 (m, 8 aromat. H and 6-H), 8.65 (s, 2-H).

b) 4-Chloro-7-(2'-deoxy-β-D-erythro-pentofuranosyl)-7H-pyrrolo[2,3-d]pyrimidine 2.4 g. (4.7 mMole) of the compound of Example 24a) are stirred for 24 hours at ambient temperature in 100 ml. methanol saturated with ammonia. The solution is evaporated to dryness, the residue is adsorbed on 10 g. silica gel 60 H and applied to a silica gel column (4×10 cm., chloroform/methanol 95:5 v/v). The product is isolated from the main fraction as a colourless, solid substance which crystallises from ethyl acetate as colourless needles. Yield 1.07 g. (84% of theory); m.p. 162° C.

TLC (chloroform/methanol, 9:1 v/v): $R_f$=0.6.

UV (methanol): $\lambda_{max.}$=273 nm (log ε=3.69).

$^1$H-NMR (DMSO-d$_6$): δ=2.28 (m, 2'-Hb), 2.58 (m, 2'-Ha), 3.57 (m, 5'-H), 3.87 (m, 4'-H), 4.40 (m, 3'-H), 5.00 (t, J=5.4 Hz, 5'-OH), 5.35 (d, J=4.2 Hz, 3'-OH), 6.66 (m, 1'-H), 6.72 (d, J=3.8 Hz, 5-H), 7.99 (d, J=3.8 Hz, 6-H), 8.66 (s, 2-H).

c) 4-Chloro-7-(2'-deoxy-β-D-erythro-pentofuranosyl)-5'-0-(4,4'-dimethoxytrityl)-7H-pyrrolo[2,3-d]-pyrimidine 1 g. (3.7 mMole) of the compound of Example 24b) is dried by evaporating with 10 ml. dry pyridine. The material is dissolved in 20 ml. dry pyridine. 2 ml. (11.7 mMole) H ünig's base and 2 g. (5.9 mMole) 4,4'-dimethoxytrityl chloride are added thereto. The solution is stirred for 3 hours at ambient temperature. After the addition of 80 ml. 5% aqueous sodium bicarbonate solution, the solution is extracted three times with 100 ml. amounts of dichloromethane. The combined organic phases are dried over anhydrous sodium sulphate. After filtering off, the filtrate is evaporated in a vacuum. The residue is purified by column chromatography (silica gel, elution agent dichloromethane and dichloromethane/ethyl acetate 9:1 v/v). Isolation of the product from the main fraction, dissolving in diethyl ether and precipitation with petroleum ether gives 1.66 g. (78% of theory) of the desired product in the form of a yellowish amorphous substance.

Analysis for $C_{32}H_{30}N_3O_5Cl$ (M.W. 572.1) calc.: C, 67.19; H, 5.29; Cl, 6.20; N, 7.35; found: 67.03; 5.47; 6.19; 7.29.

TLC (dichloromethane/acetone 9:1 v/v): $R_f$=0.3.

UV (methanol): $\lambda_{max.}$=274 nm (log $\epsilon$=3.85).

$^1$H-NMR (DMSO-d$_6$): =2.36 (m, 2'-H$_b$), 2.70 (m, 2'-H$_a$), 3.72 (s, OCH$_3$), 3.18 (d, J=4.5 Hz, 5'-H), 3.99 (m, 4'-H), 4.45 (m, 3'-H), 5.42 (d, J=4.6 Hz, 3'-OH), 6.65 (m, 1'-H), 6.69 (d, J=3.7 Hz, 5-H), 7.81 (d, J=3.7 Hz, 6-H), 8.64 (s, 2-H).

d) 4-Chloro-7-(2'-deoxy-β-D-erythro-pentofuranosyl)-5'-0-(4,4'-dimethoxytrityl)-3'-0-phenoxythiocarbonyl-7H-pyrrolo[2,3-d]pyrimidine 1 g. (1.7 mMole) of the compound of Example 24c) is dissolved in 30 ml. dry acetonitrile, 500 mg. (4.1 mMole) 4-dimethylaminopyridine and 400 μl (2.9 mMole) phenyl chlorothiocarbonate are added thereto and the solution is stirred for 16 hours at ambient temperature. Subsequently, the reaction mixture is evaporated to dryness in a vacuum and the residue applied to a silica gel column (3×15 cm., dichloromethane). From the main fraction, there are isolated 950 mg. (76% of theory) of colourless, amorphous product.

Analysis for $C_{39}H_{34}ClN_3O_6S$ (M.W. 708.2)

calc.: C, 66.14; H, 4.84; Cl, 5.01; N, 5.93; S, 4.53;

found: 66.22; 4.94; 5.12; 5.93; 4.46.

TLC (dichloromethane/acetone 95:5 v/v): $R_f$=0.8.

UV (methanol): $\lambda_{max.}$=274 nm (log $\epsilon$=3.87).

$^1$H-NMR (DMSO-d$_6$): δ=2.84 (m, 2'-H$_b$), 3.21 (m, 2'-H$_a$), 3.37 (m, 5'-H), 4.46 (m, 4'-H), 5.92 (m, 3'-H), 6.70 (m, 1'-H), 6.76 (d, J=3.8 Hz, 5-H), 7.85 (d, J=3.8 Hz, 6-H), 8.61 (s, 2-H).

e) 4-Chloro-7-(2',3'-dideoxy-β-D-glyceropentofuranosyl)-5'-0-(4,4'-dimethoxytrityl)-7H-pyrrolo-[2,3-d]pyrimidine 800 mg. (1.1 mMole) of the compound of Example 24d) and 40 mg. (0.2 mMole) 2,2'-azo-bis-(2-methyl)-propionitrile are dissolved in 40 ml. dry toluene under an atmosphere of argon. 600 μl. (2.2 mMole) tri-n-butyl stannane are added thereto, while stirring, and the reaction is continued for 2 hours at 75° C. The solvent is removed in a vacuum and the residue chromatographed on silica gel (column 15×3 cm., dichloromethane/ethyl acetate 95:5 v/v). From the main fraction, there are obtained 470 mg. (75% of theory) of the desired product.

Analysis for $C_{32}H_{30}ClN_3O_4$ (M.W. 556.1) calc.: C, 69.12; H, 5.44; Cl, 6.38; N, 7.56; found: 69.07; 5.53; 6.33; 7.58.

TLC (dichloromethane/acetone 95:5 v/v): $R_f$=0.5.

UV (methanol): $\lambda_{max.}$=273 nm (log $\epsilon$=3.78).

$^1$H-NMR (DMSO-d$_6$): δ=2.08 (m, 3'-H), 2.10 (m, 2'-H$_b$), 2.43 (m, 2'-H$_a$), 3.11 (d, J=4.4 Hz, 5'-H), 3.71 (s, OCH$_3$), 4.27 (m, 4'-H), 6.55 (dd, J=3.6 and 6.9 Hz, 1'-H), 6.64 (d, J=3.7 Hz, 5-H), 7.83 (d, J=3.7 Hz, 6-H), 8.67 (s, 2-H).

f) 4-Chloro-7-(2',3'-dideoxy-β-D-glyceropentofuranosyl)-7H-pyrrolo[2,3-d]pyrimidine 400 mg. (0.7 mMole) of the compound of Example 24e) are dissolved in 15 ml. 80% aqueous acetic acid and stirred for 30 minutes at ambient temperature. The solvent is removed in a vacuum and traces of acetic acid are removed by evaporation with water. The residue is purified by column chromatography (dichloromethane and dichloromethane/methanol, 98:2 v/v). From the main fraction there are obtained 120 mg. (67% of theory) of product which, after crystallisation from ethyl acetate, is obtained in the form of colourless needles; m.p. 90° C.

Analysis for $C_{11}H_{12}ClN_3O_2$ (M.W. 253.7) calc.: C, 52.08; H, 4.77; Cl, 13.98; N, 16.56; found: 52.20; 4.81; 14.04; 16.54.

TLC (dichloromethane/methanol 95:5 v/v): $R_f$=0.5.

UV (methanol): $\lambda_{max.}$=274 nm (log $\epsilon$=3.65).

$^1$H-NMR (DMSO-d$_6$): δ=2.04 (m, 3'-H), 2.28 (m, 2'-H$_b$), 2.46 (m, 2'-H$_a$), 3.57 (m, 5'-H), 4.11 (m, 4'-H), 4.95 (t, J=5.5 Hz, 5'-OH), 6.52 (dd, J=3.8 and 6.9 Hz, 1'-H), 6.69 (d, J=3.8 Hz, 5-H), 8.01 (d, J=3.8 Hz, 6-H), 8.64 (s, 2-H).

g) 7-(2',3'-Dideoxy-β-D-glyceropentofuranosyl)-7H-pyrrolo[2,3-d]pyrimidine

A solution of 200 mg. (0.8 mMole) of the compound of Example 24f) in 20 ml. methanol, to which had been added 0.5 ml. (6.6 mMole) of concentrated aqueous ammonia solution, is stirred with palladium on animal charcoal (40 mg., 10% Pd) in an atmosphere of hydrogen at ambient temperature for 3 hours. The catalyst is filtered off and the solvent removed in a vacuum. The residue is dissolved in water and chromatographed on an Amberlite XAD-4 column (1st elution agent water, 2nd elution agent water/methanol 8:2 v/v). Isolation of the product from the main zone gives 130 mg. (75% of theory) of the colourless product in the form of needles; m.p. 131° C.

Analysis for $C_{11}H_{13}O_2N_3$ (M.W. 219.2) calc.: C, 60.26; H, 5.98; N, 19.17; found: 60.19; 5.97; 19.18.

TLC (dichloromethane/methanol 9:1 v/v): $R_f$=0.6.

UV (methanol): $\lambda_{max.}$=270 nm (log $\epsilon$=3.56).

$^1$H-NMR (DMSO-d$_6$): δ=2.06 (m, 3'-H), 2.27 (m, 2'-H$_b$), 2.42 (m, 2'-H$_a$), 3.55 (m, 5'-H), 4.09 (m, 4'-H), 4.93 (t, J=5.5 Hz, 5'-OH), 6.54 (dd, J=4.3 and 6.9 Hz, 1'-H), 6.67 (d, J=3.7 Hz, 5-H), 7.86 (d, J=3.7 Hz, 6-H), 8.79 (s, 4-H), 9.01 (s, 2-H).

h) 4-Amino-7-(2',3'-dideoxy-β-D-glyceropentofuranosyl)-7H-pyrrolo[2,3-d]pyrimidine (2',3'-dideoxy-tubercidin)

200 mg. (0.8 mMole) of the compound of Example 24f) are stirred in 60 ml. 25% aqueous ammonia solution for 15 hours at 100° C. under pressure in a steel bomb. The solvent is subsequently removed in a vacuum and the residue dissolved in 200 ml. water. This solution is purified on Dowex 1×2 (OH$^-$ form). The column is washed with water and the product eluted with water/methanol (9:1 v/v). From the main zone are obtained 120 mg. (65% of theory) of product.

TLC (dichloromethane/methanol 9:1 v/v): $R_f$=0.3.

$^1$H-NMR (DMSO-d$_6$): δ=2.03 (m, 3'-H), 2.22 (m, 2'-H$_a$), 2.33 (m, 2'-H$_b$), 3.53 (m, 5'-H), 4.04 (m, 4'-H), 4.99 (m, 5'-OH), 6.35 (m, 1'-H), 6.51 (d, J=3.6 Hz, 5-H), 7.00 (s, NH$_2$), 7.34 (d, J=3.6 Hz, 6-H), 8.04 (s, 2-H).

i) 7-(2',3'-Dideoxy-β-D-glyceropentofuranosyl)-4-methoxy-7H-pyrrolo[2,3-d]pyrimidine 170 mg. (0.7 mMole) of the compound of Example 24f) are dissolved in 5 ml. 1M methanolic methanolate solution and stirred at ambient temperature for 4 hours. The solution is neutralised with 80% acetic acid, evaporated in a vacuum and the residue applied to a silica gel column (elution agent dichloromethane/methanol 98:2 v/v). Isolation of the main zone gives a colourless oil which, upon storing, crystallises in the form of needles. Yield 130 mg. (78% of theory).

j) 7-(2',3'-Dideoxy-β-D-glyceropentofuranosyl)-4H-pyrrolo[2,3-d]pyrimidin-4-one 200 mg. (0.8 mMole) of the compound of Example 24f) are suspended in 10 ml. 2N aqueous sodium hydroxide solution and boiled under reflux for 5 hours. The solution is neutralised with 80% acetic acid and the insoluble material is removed by filtration. The filtrate is applied to an Amberlite XAD-4 column. The column is washed with 500 ml. of water and the product eluted with water/isopropanol (9:1 v/v). There are obtained 180 mg. (80% of theory) of product.

EXAMPLE 25

1-(2',3'-Dideoxy-β-D-glyceropentafuranosyl)-1H-pyrazolo[3.4-d]pyrimidin-4-one

The product of Example 17d) is deaminated with adenosine deaminase from intestinal calf mucosa cells. The progress of the reaction is monitored UV spectro-scopically at 275 nm. The reaction gives the product quantitatively in the form of colourless crystals; m.p. 171° C.

UV (methanol): $\lambda_{max.}$=251 nm ($\epsilon$=7700).

TLC (silica gel, dichloromethane/methanol 9:1 v/v): $R_f$=0.5.

$^{13}$C-NMR ([D$_6$]DMSO): δ=135.2 (C-8), 106.1 (C-5), 157.3 (C-6), 148.4 (C-2), 152.3 (C-4), 84.6 (C-1'), 30.7 (C-2'), 27.3 (C-3'), 82.2 (C-4'), 64.2 (C-5').

$^1$H-NMR ([D$_6$]DMSO): δ=2.13 (m, 3'-H), 2.40 (m, 2'-H), 3.40 (m, 5'-H), 4.09 (m, 4'-H), 4.73 (m, 5'-OH), 6.43 (m, 1'-H), 8.11 (s, 3-H), 8.13 (s, 6-H).

EXAMPLE 26

2-Amino-7-deaza-2',3'-didesoxy-9-β-D-ribofuranosylpurine-6-one 5'-triphosphate

Analysis for C$_{11}$H$_{14}$H$_4$O$_{12}$P$_3$Na$_3$ (M.W. 556.2) calc.: P, 16.7; found: 16.4.

UV (buffer, pH 7.0): $\lambda_{max.}$=259 nm ($\epsilon$=13400)

$^{31}$P-NMR (D$_2$O): δ=−8.35 (d, P-γ), −10.0 (d, P-α), −21.5 (t, P-β).

EXAMPLE 27

2-Amino-3,7-dideaza-2'-deoxy-9-β-D-ribofuranosylpurin-6-one 5'-triphosphate

Analysis for C$_{12}$H$_{15}$N$_3$O$_{13}$P$_3$Na$_3$ (M.W. 555.2) calc.: P, 16.75; found: 16.5.

UV (buffer, pH 7.0): $\lambda_{max.}$=272 nm ($\epsilon$=12400).

EXAMPLE 28

3,7-Dideaza-2',3'-dideoxy-9-β-D-ribofuranosylpurine 5'-triphosphate

Analysis for C$_{12}$H$_{14}$N$_2$O$_{11}$P$_3$Na$_3$ (M.W. 524.1) calc.: P, 17.7; found: 17.3.

UV (buffer, pH 7.0): $\lambda_{max.}$=224, 274 nm.

All of the triphosphates described in Examples 26 to 28 are prepared by phosphorylation of the corresponding nucleosides by the method described by Yoshikawa (Tetrahedron Letters, 50, 5065/1967) to give the 5'-monophosphates and subsequent conversion into the 5'-triphosphates by the method of Hoard and Ott (J.A.C.S., 87, 1785/1965).

EXAMPLE 29

Antiviral Activity

The stability of the N-glycosidic bond of 2',3'-didesoxynucleosides is bound up with the antiviral activity.

The hydrolysis of the bond was investigated at 25° C. in three different concentrations of hydrochloric acid. For this purpose, the UV absorption (E$_t$) was measured at 258 nm. Via the absorption/time curve, there were determined the velocity constants of the hydrolysis (k) and the half life times (T/2) on the basis of the following equation:

$$k=1/t\times\ln(E_o-E_{oo})/(E_t-E_{oo})$$

E$_o$ being the absorption at time t=0 and E$_{oo}$ being the absorption after complete termination of the reaction.

There were compared 2',3'-dideoxyadenosine (a) and 6-amino-8-aza-7-deaza-2',3'-dideoxy-9-β-D-ribofuranosylpurine (b) at 25° C. The results obtained are set out in the following Table:

TABLE

|     |     | 1 N HCl | 0.1 N HCl | 0.01 N HCl |
|-----|-----|---------|-----------|------------|
| (a) | T/2 | —       | 1.9 min.  | 31.5 min.  |
|     | k   | —       | 0.363 min$^{-1}$ | 0.022 min$^{-1}$ |
| (b) | T/2 | 0.83 min. | 20.4 min. | 280 min. |
|     | k   | 0.85 min$^{-1}$ | 0.033 min$^{-1}$ | 0.0025 min$^{-1}$ |

The above Table shows that the compound (b) according to the present invention is more than 10 times more stable and thus more antivirally effective than (a).

EXAMPLE 30

Experimental Data Concerning the Stability of the Inventive Compounds

The determination of the stability of the N-glycosidic bond was carried out under acidic conditions by measuring the UV-absorbance as a function of time. The compounds were classified as stable, when no hydrolysis occurred within the hydrolysis time of the corresponding purine-derivatives.

The following abbreviations were used:
c$^7$z$^8$=pyrazolo[3,4-d]pyrimidine
c$^3$c$^7$=pyrrolo[3,2-0]pyridine
c$^7$=pyrrolo[2,3-d]pyrimidine.

Table of kinetic data with respect to hydrolysis of nucleosides: (half life [t(½)] in minutes)

| Compound | 1 N HCL | 0.1 N HCL | 0.01 N HCL |
|----------|---------|-----------|------------|
| ddA      | —       | 1.9       | 31.5       |
| c$^7$z$^8$ddA | — | 20.4     | 280        |
| c$^3$c$^7$ddA | stable | stable | stable    |
| c$^7$ddA | stable  | stable    | stable     |
| ddG      | —       | —         | 37         |
| c$^7$z$^8$ddG | — | —        | 135        |
| c$^7$ddG | stable  | stable    | stable     |

The higher degree of stability of the inventive compounds allows for longer durability, when the compounds are dissolved in aqueous solution and shipped or stored for a longer period of time. Additionally, the inventive compounds, especially the nucleosides (Y=H) have the advantage, that it is easier to convert these compounds into the corresponding nucleotides (Y=mono-, di-or triphosphate). The phosphorylation is usually carried out with POCl$_3$ whereby hydrochloric acid is liberated, which is bound in the reaction solution as pyridinium-hydrochloride. Pyridinium-hydrochloride and hydrochloric acid both lead to hydrolysis of the N-glycosidic bond in case of the ribonucleosides and a significant reduction in the yield of the corresponding nucleotides can be observed. Therefore, additional steps must be taken during synthesis of the nucleotides by inserting additional protection groups. Such steps are not necessary in case of the inventive compounds.

It will be understood that the specification and examples are illustrative but not limitative of the present invention and that other embodiments within the spirit and scope of the invention will suggest themselves to those skilled in the art.

We claim:

1. The compound 2-amino-7-deaza-2',3'-dideoxy-9-beta-D-ribofuranosyl-purine-6-one or a triphosphate thereof, in the form of a solution.

2. Reagent for determining a nucleic acid sequence comprising the compound 2-amino-7-deaza-2',3'-dideoxy-9-beta-D-ribofuranosyl-purine-6-one or a triphosphate thereof and a nucleotide selected from the group adenosine, thymidine, cytosine and guanosine.

* * * * *

UNITED STATES PATENT AND TRADEMARK OFFICE
CERTIFICATE OF CORRECTION

PATENT NO. : 6,211,158 B1
DATED : April 3, 2001
INVENTOR(S) : Seela, et al.

It is certified that error appears in the above-identified patent and that said Letters Patent is hereby corrected as shown below:

Title page,
Inventors,
Change "Osnabrück" to -- Hamburg --.

Foreign Application Priority Data,
Change "14" to -- 10 --.

Column 5,
Line 23, before "deoxy" insert -- 2 --.

Column 11,
Line 61, after "10" insert -- % --.

Column 12,
Line 53, change "desaza" to -- deaza --.

Column 16,
Line 5, change "didesoxy" to -- dideoxy --.

Column 20,
Line 48, change "deox" to -- deoxy --.

Column 26,
Line 48, in the Table, change "in minutes" to -- at 25° C --.
Line 57, column 1, change "c7ddG" to -- c7ddC --.

Signed and Sealed this

Twenty-third Day of October, 2001

NICHOLAS P. GODICI
Acting Director of the United States Patent and Trademark Office